US008788042B2

(12) United States Patent
Mercanzini et al.

(10) Patent No.: US 8,788,042 B2
(45) Date of Patent: Jul. 22, 2014

(54) APPARATUS AND METHOD FOR OPTIMIZED STIMULATION OF A NEUROLOGICAL TARGET

(75) Inventors: Andre Mercanzini, Renens (CH); Philippe Renaud, Preverenges (CH)

(73) Assignee: Ecole Polytechnique Federale de Lausanne (EPFL), Lausanne (CH)

(*) Notice: Subject to any disclaimer, the term of this patent is extended or adjusted under 35 U.S.C. 154(b) by 468 days.

(21) Appl. No.: 13/056,261

(22) PCT Filed: Jul. 29, 2009

(86) PCT No.: PCT/US2009/052077
§ 371 (c)(1),
(2), (4) Date: May 9, 2011

(87) PCT Pub. No.: WO2010/014686
PCT Pub. Date: Feb. 4, 2010

(65) Prior Publication Data
US 2011/0295350 A1 Dec. 1, 2011

Related U.S. Application Data

(60) Provisional application No. 61/084,870, filed on Jul. 30, 2008.

(51) Int. Cl.
A61N 1/05 (2006.01)
A61N 1/36 (2006.01)
A61B 5/00 (2006.01)
A61B 5/04 (2006.01)
A61B 5/053 (2006.01)

(52) U.S. Cl.
CPC ............ *A61N 1/0531* (2013.01); *A61N 1/0534* (2013.01); *A61N 1/36185* (2013.01); *A61B 5/4094* (2013.01); *A61B 5/04001* (2013.01); *A61B 5/0031* (2013.01); *A61N 1/36082* (2013.01); *A61B 5/053* (2013.01)
USPC ..................... 607/45; 607/2; 607/1

(58) Field of Classification Search
CPC A61N 1/0534; A61N 1/36185; A61N 1/0529
USPC .......................................... 607/45
See application file for complete search history.

(56) References Cited

U.S. PATENT DOCUMENTS 4,245,645 A 1/1981 Arseneault et al.
4,550,733 A 11/1985 Liss et al.
(Continued)

FOREIGN PATENT DOCUMENTS

EP 0 677 743 10/1995
EP 0 743 839 11/1996
(Continued)

OTHER PUBLICATIONS

PCT International Search Report and Written Opinion—(PCT/US2009/052077) Date of Mailing Sep. 25, 2009.
(Continued)

*Primary Examiner* — Christopher D Koharski
*Assistant Examiner* — Philip Edwards
(74) *Attorney, Agent, or Firm* — Foley & Lardner LLP

(57) ABSTRACT

A preferred frequency is identified, being usable to stimulate a neurological target within a mammalian body using at least one microelectrode positioned at or near the target. To establish efficient and effective stimulation, an impedance analyzer is provided for measuring electrical impedance values indicative of a microelectrode-tissue interface across a range of different frequencies. A preferred one of the measured electrical impedance values is identified as being closest to a pure resistance. The neurological target can then be stimulated at or near the frequency associated with the preferred impedance value (peak resistance frequency), thereby promoting desirable traits, such as optimum charge transfer, minimum signal distortion, increased stimulation efficiency, and prevention of microelectrode corrosion. The peak resistance frequency can be used to determine an preferred pulse shape. A target can be identified by microelectrode measurements of neuronal activity and/or impedance magnitude at peak resistance frequency.

10 Claims, 20 Drawing Sheets

(56) References Cited

U.S. PATENT DOCUMENTS

| | | |
|---|---|---|
| 4,837,049 A | 6/1989 | Byers et al. |
| 4,917,093 A | 4/1990 | Dufresne et al. |
| 4,969,468 A | 11/1990 | Byers et al. |
| 5,215,088 A | 6/1993 | Normann et al. |
| 5,391,250 A | 2/1995 | Cheney et al. |
| 5,419,777 A | 5/1995 | Hofling |
| 5,496,369 A | 3/1996 | Howard, III |
| 5,628,317 A | 5/1997 | Starkebaum et al. |
| 5,643,330 A | 7/1997 | Holsheimer et al. |
| 5,683,422 A | 11/1997 | Rise |
| 5,697,651 A | 12/1997 | Fernandes |
| 5,697,975 A | 12/1997 | Howard et al. |
| 5,702,429 A | 12/1997 | King |
| 5,713,922 A | 2/1998 | King |
| 5,713,923 A | 2/1998 | Ward et al. |
| 5,716,377 A | 2/1998 | Rise et al. |
| 5,727,552 A | 3/1998 | Ryan |
| 5,752,979 A | 5/1998 | Benabid |
| 5,782,798 A | 7/1998 | Rise |
| 5,792,186 A | 8/1998 | Rise |
| 5,797,970 A | 8/1998 | Pouvreau |
| 5,800,474 A | 9/1998 | Benabid et al. |
| 5,800,535 A | 9/1998 | Howard, III |
| 5,814,092 A | 9/1998 | King |
| 5,824,029 A | 10/1998 | Weijand et al. |
| 5,833,709 A | 11/1998 | Rise et al. |
| 5,833,714 A | 11/1998 | Loeb |
| 5,843,148 A | 12/1998 | Gijsbers et al. |
| 5,893,883 A | 4/1999 | Torgerson et al. |
| 5,913,882 A | 6/1999 | King |
| 5,927,277 A | 7/1999 | Baudino et al. |
| 5,941,906 A | 8/1999 | Barreras et al. |
| 5,957,958 A | 9/1999 | Schulman et al. |
| 5,975,085 A | 11/1999 | Rise |
| 5,978,702 A | 11/1999 | Ward et al. |
| 5,991,668 A | 11/1999 | Leinders et al. |
| 6,011,996 A | 1/2000 | Gielen et al. |
| 6,018,682 A | 1/2000 | Rise |
| 6,038,480 A | 3/2000 | Hrdlicka et al. |
| 6,050,992 A | 4/2000 | Nichols |
| 6,104,960 A | 8/2000 | Duysens et al. |
| 6,109,269 A | 8/2000 | Rise et al. |
| 6,125,300 A | 9/2000 | Weijand et al. |
| 6,128,537 A | 10/2000 | Rise |
| 6,161,047 A | 12/2000 | King et al. |
| 6,205,359 B1 | 3/2001 | Boveja |
| 6,205,361 B1 | 3/2001 | Kuzma et al. |
| 6,216,043 B1 | 4/2001 | Swanson et al. |
| 6,227,203 B1 | 5/2001 | Rise et al. |
| 6,253,109 B1 | 6/2001 | Gielen |
| 6,253,110 B1 | 6/2001 | Brabec et al. |
| 6,263,237 B1 | 7/2001 | Rise |
| 6,266,564 B1 | 7/2001 | Hill et al. |
| 6,295,476 B1 | 9/2001 | Schaenzer |
| 6,319,241 B1 | 11/2001 | King et al. |
| 6,330,466 B1 | 12/2001 | Hofmann et al. |
| 6,337,997 B1 | 1/2002 | Rise |
| 6,343,226 B1 | 1/2002 | Sunde et al. |
| 6,353,762 B1 | 3/2002 | Baudino et al. |
| 6,356,784 B1 | 3/2002 | Lozano et al. |
| 6,356,786 B1 | 3/2002 | Rezai et al. |
| 6,356,787 B1 | 3/2002 | Rezai et al. |
| 6,366,813 B1 | 4/2002 | DiLorenzo |
| 6,374,140 B1 | 4/2002 | Rise |
| 6,375,666 B1 | 4/2002 | Mische |
| 6,379,353 B1 | 4/2002 | Nichols |
| 6,434,431 B1 | 8/2002 | Camps et al. |
| 6,479,999 B1 | 11/2002 | DeMeester et al. |
| 6,484,059 B2 | 11/2002 | Gielen |
| 6,529,774 B1 | 3/2003 | Greene |
| 6,538,443 B2 | 3/2003 | Morich et al. |
| 6,549,812 B1 | 4/2003 | Smits |
| 6,556,873 B1 | 4/2003 | Smits |
| 6,560,472 B2 | 5/2003 | Hill et al. |
| 6,560,486 B1 | 5/2003 | Osorio et al. |
| 6,587,733 B1 | 7/2003 | Cross et al. |
| 6,591,128 B1 | 7/2003 | Wu et al. |
| 6,594,524 B2 | 7/2003 | Esteller et al. |
| 6,597,953 B2 | 7/2003 | Boling |
| 6,643,552 B2 | 11/2003 | Edell et al. |
| 6,671,544 B2 | 12/2003 | Baudino |
| 6,675,046 B2 | 1/2004 | Holsheimer |
| 6,687,538 B1 | 2/2004 | Hrdlicka et al. |
| 6,690,973 B2 | 2/2004 | Hill et al. |
| 6,708,064 B2 | 3/2004 | Rezai |
| 6,718,208 B2 | 4/2004 | Hill et al. |
| 6,718,211 B2 | 4/2004 | Smits |
| 6,741,893 B2 | 5/2004 | Smits |
| 6,745,079 B2 | 6/2004 | King |
| 6,795,737 B2 | 9/2004 | Gielen et al. |
| 6,804,552 B2 | 10/2004 | Thompson et al. |
| 6,829,498 B2 | 12/2004 | Kipke et al. |
| 6,850,802 B2 | 2/2005 | Holsheimer |
| 6,871,098 B2 | 3/2005 | Nuttin et al. |
| 6,882,881 B1 | 4/2005 | Lesser et al. |
| 6,892,097 B2 | 5/2005 | Holsheimer |
| 6,892,438 B1 | 5/2005 | Hill et al. |
| 6,904,306 B1 | 6/2005 | Wu et al. |
| 6,909,920 B2 | 6/2005 | Lokhoff et al. |
| 6,920,359 B2 | 7/2005 | Meadows et al. |
| 6,928,320 B2 | 8/2005 | King |
| 6,950,706 B2 | 9/2005 | Rodriguez et al. |
| 6,950,709 B2 | 9/2005 | Baudino |
| 6,978,171 B2 | 12/2005 | Goetz et al. |
| 6,978,178 B2 | 12/2005 | Sommer et al. |
| 6,999,819 B2 | 2/2006 | Swoyer et al. |
| 7,006,859 B1 | 2/2006 | Osorio et al. |
| 7,010,351 B2 | 3/2006 | Firlik et al. |
| 7,010,356 B2 | 3/2006 | Jog et al. |
| 7,024,246 B2 | 4/2006 | Acosta et al. |
| 7,035,690 B2 | 4/2006 | Goetz |
| 7,047,084 B2 | 5/2006 | Erickson et al. |
| 7,050,856 B2 | 5/2006 | Stypulkowski |
| 7,061,240 B2 | 6/2006 | Ham et al. |
| 7,076,292 B2 | 7/2006 | Forsberg |
| 7,077,822 B1 | 7/2006 | Howard, III |
| 7,107,104 B2 | 9/2006 | Keravel et al. |
| 7,133,718 B2 | 11/2006 | Bakken et al. |
| 7,151,961 B1 | 12/2006 | Whitehurst et al. |
| 7,174,219 B2 | 2/2007 | Wahlstrand et al. |
| 7,181,288 B1 | 2/2007 | Rezai et al. |
| 7,184,829 B2 | 2/2007 | Hill et al. |
| 7,187,978 B2 | 3/2007 | Malek et al. |
| 7,191,016 B2 | 3/2007 | Marshall et al. |
| 7,191,018 B2 | 3/2007 | Gielen et al. |
| 7,203,548 B2 | 4/2007 | Whitehurst et al. |
| 7,204,833 B1 | 4/2007 | Osorio et al. |
| 7,209,787 B2 | 4/2007 | DiLorenzo |
| 7,212,851 B2 | 5/2007 | Donoghue et al. |
| 7,212,867 B2 | 5/2007 | Van Venrooij et al. |
| 7,214,189 B2 | 5/2007 | Zdeblick |
| 7,216,000 B2 | 5/2007 | Sieracki et al. |
| 7,216,001 B2 | 5/2007 | Hacker et al. |
| 7,231,256 B2 | 6/2007 | Wahlstrand et al. |
| 7,236,822 B2 | 6/2007 | Dobak, III |
| 7,242,984 B2 | 7/2007 | DiLorenzo |
| 7,280,867 B2 | 10/2007 | Frei et al. |
| 7,282,030 B2 | 10/2007 | Frei et al. |
| 7,282,050 B2 | 10/2007 | Starkebaum et al. |
| 7,286,878 B2 | 10/2007 | Stypulkowski |
| 7,286,882 B2 | 10/2007 | Cole |
| 7,288,066 B2 | 10/2007 | Drew |
| 7,289,851 B2 | 10/2007 | Gunderson et al. |
| 7,289,852 B2 | 10/2007 | Helfinstine et al. |
| 7,295,880 B2 | 11/2007 | Gielen |
| 7,298,143 B2 | 11/2007 | Jaermann et al. |
| 7,313,430 B2 | 12/2007 | Urquhart et al. |
| 7,313,440 B2 | 12/2007 | Miesel |
| 7,315,759 B2 | 1/2008 | Markowitz et al. |
| 7,317,947 B2 | 1/2008 | Wahlstrand et al. |
| 7,317,948 B1 | 1/2008 | King et al. |
| 7,319,899 B2 | 1/2008 | Keizer |
| 7,319,904 B2 | 1/2008 | Cross et al. |
| 7,321,798 B2 | 1/2008 | Muhlenberg et al. |

(56) References Cited

U.S. PATENT DOCUMENTS

| | | |
|---|---|---|
| 7,321,837 B2 | 1/2008 | Osorio et al. |
| 7,322,832 B2 | 1/2008 | Kronich et al. |
| 7,328,057 B2 | 2/2008 | Freas et al. |
| 7,328,068 B2 | 2/2008 | Spinelli et al. |
| 7,328,069 B2 | 2/2008 | Gerber |
| 7,330,760 B2 | 2/2008 | Heruth et al. |
| 7,337,010 B2 | 2/2008 | Howard et al. |
| 7,343,206 B2 | 3/2008 | Sage et al. |
| 7,346,395 B2 | 3/2008 | Lozano et al. |
| 7,356,369 B2 | 4/2008 | Phillips et al. |
| 7,359,837 B2 | 4/2008 | Drew |
| 7,366,572 B2 | 4/2008 | Heruth et al. |
| 7,367,956 B2 | 5/2008 | King |
| 7,369,891 B2 | 5/2008 | Augustijn et al. |
| 7,369,893 B2 | 5/2008 | Gunderson |
| 7,369,894 B2 | 5/2008 | Gerber |
| 7,385,443 B1 | 6/2008 | Denison |
| 7,388,378 B2 | 6/2008 | Gray et al. |
| 7,389,147 B2 | 6/2008 | Wahlstrand et al. |
| 7,390,311 B2 | 6/2008 | Hildebrand et al. |
| 7,391,257 B1 | 6/2008 | Denison et al. |
| 7,392,089 B2 | 6/2008 | Wahlstrand et al. |
| 7,395,113 B2 | 7/2008 | Heruth et al. |
| 7,400,927 B1 | 7/2008 | Litvin |
| 7,406,351 B2 | 7/2008 | Wesselink |
| 7,418,292 B2 | 8/2008 | Shafer |
| 7,421,297 B2 | 9/2008 | Giftakis et al. |
| 7,427,280 B2 | 9/2008 | Gerber |
| 7,429,938 B1 | 9/2008 | Corndorf |
| 7,433,734 B2 | 10/2008 | King |
| 7,442,183 B2 | 10/2008 | Baudino et al. |
| 7,447,545 B2 | 11/2008 | Heruth et al. |
| 7,450,996 B2 | 11/2008 | MacDonald et al. |
| 7,463,917 B2 | 12/2008 | Martinez |
| 7,463,928 B2 | 12/2008 | Lee et al. |
| 7,474,247 B1 | 1/2009 | Heinks et al. |
| 7,479,910 B1 | 1/2009 | Heinks et al. |
| 7,483,748 B2 | 1/2009 | Torgerson et al. |
| 7,489,966 B2 | 2/2009 | Leinders et al. |
| 7,489,970 B2 | 2/2009 | Lee et al. |
| 7,491,181 B2 | 2/2009 | Heruth et al. |
| 7,497,844 B2 | 3/2009 | Spear et al. |
| 7,497,863 B2 | 3/2009 | Solar et al. |
| 7,502,217 B2 | 3/2009 | Zhao et al. |
| 7,505,815 B2 | 3/2009 | Lee et al. |
| 7,505,869 B2 | 3/2009 | Hartlaub |
| 7,515,961 B2 | 4/2009 | Germanson et al. |
| 7,519,431 B2 | 4/2009 | Goetz et al. |
| 7,519,432 B2 | 4/2009 | Bolea et al. |
| 7,526,339 B2 | 4/2009 | Lahti et al. |
| 7,526,340 B2 | 4/2009 | Drew |
| 7,526,341 B2 | 4/2009 | Goetz et al. |
| 7,529,582 B1 | 5/2009 | DiLorenzo |
| 7,529,586 B2 | 5/2009 | Wahlstrand et al. |
| 7,542,803 B2 | 6/2009 | Heruth et al. |
| 7,546,164 B2 | 6/2009 | King |
| 7,546,166 B2 | 6/2009 | Michels et al. |
| 7,548,775 B2 | 6/2009 | Kipke et al. |
| 7,548,786 B2 | 6/2009 | Lee et al. |
| 7,551,951 B1 | 6/2009 | Osorio et al. |
| 7,551,960 B2 | 6/2009 | Forsberg et al. |
| 7,555,345 B2 | 6/2009 | Wahlstrand et al. |
| 7,561,921 B2 | 7/2009 | Phillips et al. |
| 7,563,141 B2 | 7/2009 | Alexander et al. |
| 7,563,541 B2 | 7/2009 | Howard et al. |
| 7,578,819 B2 | 8/2009 | Bleich et al. |
| 7,580,756 B2 | 8/2009 | Schulte et al. |
| 7,582,387 B2 | 9/2009 | Howard et al. |
| 7,590,451 B2 | 9/2009 | Tronnes et al. |
| 7,590,453 B2 | 9/2009 | Heruth et al. |
| 7,590,455 B2 | 9/2009 | Heruth et al. |
| 7,591,970 B2 | 9/2009 | Olson |
| 7,594,828 B2 | 9/2009 | Alexander et al. |
| 7,594,889 B2 | 9/2009 | St. Ores et al. |
| 7,596,399 B2 | 9/2009 | Singhal et al. |
| 7,596,408 B2 | 9/2009 | Singhal et al. |
| 7,596,415 B2 | 9/2009 | Brabec et al. |
| 7,599,730 B2 | 10/2009 | Hunter et al. |
| 7,603,161 B2 | 10/2009 | Wurmfeld et al. |
| 7,603,177 B2 | 10/2009 | Sieracki et al. |
| 7,604,629 B2 | 10/2009 | Gerber et al. |
| 7,604,644 B2 | 10/2009 | Schulte et al. |
| 7,608,458 B2 | 10/2009 | Soykan et al. |
| 7,610,083 B2 | 10/2009 | Drew et al. |
| 7,611,483 B2 | 11/2009 | Gerber et al. |
| 7,614,743 B2 | 11/2009 | Geiger |
| 7,615,015 B2 | 11/2009 | Coleman |
| 7,616,998 B2 | 11/2009 | Nuttin et al. |
| 7,617,002 B2 | 11/2009 | Goetz |
| 7,620,454 B2 | 11/2009 | Dinsmoor et al. |
| 7,622,303 B2 | 11/2009 | Soykan et al. |
| 7,622,988 B2 | 11/2009 | Denison et al. |
| 7,623,053 B2 | 11/2009 | Terry et al. |
| 7,623,918 B2 | 11/2009 | Goetz |
| 7,623,919 B2 | 11/2009 | Goetz et al. |
| 7,623,923 B2 | 11/2009 | Gerber et al. |
| 7,623,930 B2 | 11/2009 | Zeijlemaker et al. |
| 7,624,293 B2 | 11/2009 | Osorio et al. |
| 7,628,780 B2 | 12/2009 | Bonner et al. |
| 7,631,415 B2 | 12/2009 | Phillips et al. |
| 7,632,225 B2 | 12/2009 | Stypulkowski |
| 7,635,541 B2 | 12/2009 | Scott et al. |
| 7,640,059 B2 | 12/2009 | Forsberg et al. |
| 7,641,992 B2 | 1/2010 | Howard et al. |
| 7,642,013 B2 | 1/2010 | Howard et al. |
| 7,647,111 B2 | 1/2010 | Ries et al. |
| 7,647,116 B2 | 1/2010 | Bauhahn |
| 7,647,117 B2 | 1/2010 | Bauhahn |
| 7,647,121 B2 | 1/2010 | Wahlstrand et al. |
| 7,650,291 B2 | 1/2010 | Rosenfeld et al. |
| 7,653,433 B2 | 1/2010 | Lozano et al. |
| 7,657,318 B2 | 2/2010 | King et al. |
| 7,657,319 B2 | 2/2010 | Goetz et al. |
| 7,660,620 B2 | 2/2010 | Zeijlemaker et al. |
| 7,660,630 B2 | 2/2010 | Dudding et al. |
| 7,662,140 B2 | 2/2010 | Heruth et al. |
| 7,662,509 B2 | 2/2010 | Howard et al. |
| 7,664,551 B2 | 2/2010 | Cigaina |
| 7,664,552 B2 | 2/2010 | Wahlstrand et al. |
| 7,668,601 B2 | 2/2010 | Hegland et al. |
| 7,671,594 B2 | 3/2010 | Gray |
| 7,676,271 B2 | 3/2010 | Wahlstrand et al. |
| 7,676,273 B2 | 3/2010 | Goetz et al. |
| 7,676,274 B2 | 3/2010 | Hung et al. |
| 7,680,540 B2 | 3/2010 | Jensen et al. |
| 7,682,355 B2 | 3/2010 | Gerber et al. |
| 7,682,745 B2 | 3/2010 | Howard et al. |
| 7,684,860 B2 | 3/2010 | Wahlstrand et al. |
| 7,684,873 B2 | 3/2010 | Gerber |
| 7,689,289 B2 | 3/2010 | King |
| 7,697,972 B2 | 4/2010 | Verard et al. |
| 7,697,995 B2 | 4/2010 | Cross et al. |
| 7,706,124 B2 | 4/2010 | Zhao et al. |
| 7,706,889 B2 | 4/2010 | Gerber et al. |
| 7,711,421 B2 | 5/2010 | Shafer et al. |
| 7,711,428 B2 | 5/2010 | Janzig et al. |
| 7,711,436 B2 | 5/2010 | Stone |
| 7,720,548 B2 | 5/2010 | King |
| 7,729,780 B2 | 6/2010 | Vardiman |
| 7,742,823 B2 | 6/2010 | King et al. |
| 7,756,588 B2 | 7/2010 | Jog et al. |
| 7,797,029 B2 | 9/2010 | Gibson et al. |
| 7,822,483 B2 | 10/2010 | Stone et al. |
| 7,853,303 B2 | 12/2010 | Nikumb et al. |
| 7,899,539 B2 | 3/2011 | Whitehurst et al. |
| 7,930,035 B2 | 4/2011 | DiLorenzo |
| 7,941,202 B2 | 5/2011 | Hetke et al. |
| 7,945,336 B2 | 5/2011 | Sauter-Starace et al. |
| 7,979,105 B2 | 7/2011 | Kipke et al. |
| 8,000,794 B2 | 8/2011 | Lozano |
| 8,000,808 B2 | 8/2011 | Hegland et al. |
| 8,032,224 B2 | 10/2011 | Miesel et al. |
| 8,036,737 B2 | 10/2011 | Goetz et al. |
| 8,099,170 B2 | 1/2012 | Jensen et al. |

(56) References Cited

U.S. PATENT DOCUMENTS

| | | |
|---|---|---|
| 8,280,514 B2 | 10/2012 | Lozano et al. |
| 2002/0062143 A1 | 5/2002 | Baudino et al. |
| 2003/0004553 A1 | 1/2003 | Grill et al. |
| 2003/0023282 A1 | 1/2003 | Barrett et al. |
| 2003/0036780 A1 | 2/2003 | Barrett et al. |
| 2003/0100823 A1 | 5/2003 | Kipke et al. |
| 2003/0176892 A1 | 9/2003 | Shalev |
| 2004/0002635 A1 | 1/2004 | Hargrove et al. |
| 2004/0015205 A1 | 1/2004 | Whitehurst et al. |
| 2004/0102828 A1 | 5/2004 | Lowry et al. |
| 2004/0122335 A1 | 6/2004 | Sackellares et al. |
| 2004/0133390 A1 | 7/2004 | Osorio et al. |
| 2004/0138517 A1 | 7/2004 | Osorio et al. |
| 2004/0138536 A1 | 7/2004 | Frei et al. |
| 2004/0138720 A1 | 7/2004 | Naisberg et al. |
| 2004/0138722 A1 | 7/2004 | Carroll et al. |
| 2004/0152958 A1 | 8/2004 | Frei et al. |
| 2004/0172089 A1 | 9/2004 | Whitehurst et al. |
| 2004/0215288 A1 | 10/2004 | Lee et al. |
| 2004/0225335 A1 | 11/2004 | Whitehurst et al. |
| 2004/0249417 A1 | 12/2004 | Ransbury et al. |
| 2005/0004627 A1 | 1/2005 | Gibson et al. |
| 2005/0008660 A1 | 1/2005 | Kipke et al. |
| 2005/0010261 A1 | 1/2005 | Luders et al. |
| 2005/0027284 A1 | 2/2005 | Lozano et al. |
| 2005/0049655 A1 | 3/2005 | Boveja et al. |
| 2005/0070971 A1 | 3/2005 | Fowler et al. |
| 2005/0075681 A1 | 4/2005 | Rezai et al. |
| 2005/0113882 A1 | 5/2005 | Cameron et al. |
| 2005/0143790 A1 | 6/2005 | Kipke et al. |
| 2005/0154425 A1 | 7/2005 | Boveja et al. |
| 2005/0171558 A1 | 8/2005 | Abovitz et al. |
| 2005/0182455 A1 | 8/2005 | Thrope et al. |
| 2005/0209511 A1 | 9/2005 | Heruth et al. |
| 2005/0209513 A1 | 9/2005 | Heruth et al. |
| 2005/0209643 A1 | 9/2005 | Heruth et al. |
| 2005/0240242 A1* | 10/2005 | DiLorenzo ............... 607/45 |
| 2005/0245988 A1 | 11/2005 | Miesel |
| 2006/0004422 A1 | 1/2006 | De Ridder |
| 2006/0030897 A1 | 2/2006 | Gilmer et al. |
| 2006/0049957 A1 | 3/2006 | Surgenor et al. |
| 2006/0058727 A1 | 3/2006 | Bernabei |
| 2006/0058855 A1 | 3/2006 | Gill |
| 2006/0095105 A1 | 5/2006 | Jog et al. |
| 2006/0129203 A1 | 6/2006 | Garabedian et al. |
| 2006/0135877 A1 | 6/2006 | Giftakis et al. |
| 2006/0149337 A1 | 7/2006 | John |
| 2006/0167497 A1 | 7/2006 | Armstrong et al. |
| 2006/0173263 A1 | 8/2006 | He et al. |
| 2006/0173510 A1 | 8/2006 | Besio et al. |
| 2006/0178709 A1 | 8/2006 | Foster et al. |
| 2006/0195154 A1 | 8/2006 | Jaax et al. |
| 2006/0212090 A1 | 9/2006 | Lozano et al. |
| 2006/0241717 A1 | 10/2006 | Whitehurst et al. |
| 2006/0258951 A1 | 11/2006 | Bleich et al. |
| 2006/0264777 A1 | 11/2006 | Drew |
| 2006/0276866 A1 | 12/2006 | McCreery |
| 2006/0282014 A1 | 12/2006 | Kipke et al. |
| 2006/0293720 A1 | 12/2006 | DiLorenzo |
| 2006/0293721 A1 | 12/2006 | Tarver et al. |
| 2007/0027498 A1 | 2/2007 | Maschino et al. |
| 2007/0027500 A1 | 2/2007 | Maschino et al. |
| 2007/0027514 A1 | 2/2007 | Gerber |
| 2007/0043268 A1 | 2/2007 | Russell |
| 2007/0060974 A1 | 3/2007 | Lozano |
| 2007/0067002 A1 | 3/2007 | Lozano |
| 2007/0067003 A1 | 3/2007 | Sanchez et al. |
| 2007/0088403 A1 | 4/2007 | Wyler et al. |
| 2007/0088404 A1 | 4/2007 | Wyler et al. |
| 2007/0093870 A1 | 4/2007 | Maschino |
| 2007/0100389 A1 | 5/2007 | Jaax et al. |
| 2007/0100392 A1 | 5/2007 | Maschino et al. |
| 2007/0100393 A1 | 5/2007 | Whitehurst et al. |
| 2007/0100398 A1 | 5/2007 | Sloan |
| 2007/0106143 A1 | 5/2007 | Flaherty |
| 2007/0123765 A1 | 5/2007 | Hetke et al. |
| 2007/0142872 A1 | 6/2007 | Mickle et al. |
| 2007/0150024 A1 | 6/2007 | Leyde et al. |
| 2007/0173890 A1 | 7/2007 | Armstrong |
| 2007/0173901 A1 | 7/2007 | Reeve |
| 2007/0173908 A1 | 7/2007 | Begnaud |
| 2007/0179558 A1 | 8/2007 | Gliner et al. |
| 2007/0185544 A1 | 8/2007 | Dawant et al. |
| 2007/0197892 A1 | 8/2007 | Shen et al. |
| 2007/0203537 A1 | 8/2007 | Goetz et al. |
| 2007/0203546 A1 | 8/2007 | Stone et al. |
| 2007/0208394 A1 | 9/2007 | King et al. |
| 2007/0213784 A1 | 9/2007 | Pless |
| 2007/0213785 A1 | 9/2007 | Osorio et al. |
| 2007/0213786 A1 | 9/2007 | Sackellares et al. |
| 2007/0225674 A1 | 9/2007 | Molnar et al. |
| 2007/0225773 A1 | 9/2007 | Shen et al. |
| 2007/0225774 A1 | 9/2007 | Eskandar et al. |
| 2007/0233192 A1 | 10/2007 | Craig |
| 2007/0249953 A1 | 10/2007 | Frei et al. |
| 2007/0249954 A1 | 10/2007 | Virag et al. |
| 2007/0250133 A1 | 10/2007 | Carlson et al. |
| 2007/0255323 A1 | 11/2007 | Werder et al. |
| 2007/0255338 A1 | 11/2007 | Wahlstrand |
| 2007/0255374 A1 | 11/2007 | Kolafa et al. |
| 2007/0255531 A1 | 11/2007 | Drew |
| 2007/0265683 A1 | 11/2007 | Ehrlich |
| 2007/0282389 A1 | 12/2007 | Moxon et al. |
| 2008/0021514 A1 | 1/2008 | Pless |
| 2008/0021517 A1 | 1/2008 | Dietrich |
| 2008/0027487 A1 | 1/2008 | Patel et al. |
| 2008/0027503 A1 | 1/2008 | Marrosu et al. |
| 2008/0027504 A1 | 1/2008 | Bedenbaugh |
| 2008/0039895 A1 | 2/2008 | Fowler et al. |
| 2008/0046012 A1 | 2/2008 | Covalin et al. |
| 2008/0046013 A1 | 2/2008 | Lozano |
| 2008/0077186 A1 | 3/2008 | Thompson et al. |
| 2008/0077191 A1 | 3/2008 | Morrell |
| 2008/0103547 A1 | 5/2008 | Okun et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0139870 A1 | 6/2008 | Gliner et al. |
| 2008/0154331 A1 | 6/2008 | John et al. |
| 2008/0161896 A1 | 7/2008 | Sauter-Starace et al. |
| 2008/0172103 A1 | 7/2008 | Kao et al. |
| 2008/0188905 A1 | 8/2008 | Swartz |
| 2008/0195166 A1 | 8/2008 | Sun et al. |
| 2008/0195227 A1 | 8/2008 | Boling et al. |
| 2008/0208283 A1 | 8/2008 | Vetter et al. |
| 2008/0208287 A1 | 8/2008 | Palermo et al. |
| 2008/0215125 A1 | 9/2008 | Farah et al. |
| 2008/0221642 A1 | 9/2008 | Humayun et al. |
| 2008/0255647 A1 | 10/2008 | Jensen et al. |
| 2008/0269835 A1 | 10/2008 | Carlson et al. |
| 2008/0269842 A1 | 10/2008 | Giftakis et al. |
| 2008/0275526 A1 | 11/2008 | Lozano |
| 2008/0300652 A1 | 12/2008 | Lim et al. |
| 2009/0027504 A1 | 1/2009 | Lim et al. |
| 2009/0118806 A1 | 5/2009 | Vetter et al. |
| 2009/0132042 A1 | 5/2009 | Hetke et al. |
| 2009/0240314 A1 | 9/2009 | Kong et al. |
| 2009/0253977 A1 | 10/2009 | Kipke et al. |
| 2009/0292325 A1 | 11/2009 | Cederna et al. |
| 2009/0299174 A1 | 12/2009 | Wright et al. |
| 2009/0306729 A1 | 12/2009 | Doerr |
| 2009/0312770 A1 | 12/2009 | Kozai et al. |
| 2009/0325424 A1 | 12/2009 | Aarts et al. |
| 2010/0030298 A1 | 2/2010 | Martens et al. |
| 2010/0036468 A1 | 2/2010 | Decre et al. |
| 2010/0076536 A1 | 3/2010 | Merz et al. |
| 2010/0087853 A1 | 4/2010 | Kipke et al. |
| 2010/0100152 A1 | 4/2010 | Martens et al. |
| 2010/0114193 A1 | 5/2010 | Lozano et al. |
| 2010/0145216 A1 | 6/2010 | He et al. |
| 2010/0145414 A1 | 6/2010 | Decre et al. |
| 2010/0152747 A1 | 6/2010 | Padiy et al. |
| 2010/0198315 A1 | 8/2010 | Martens et al. |
| 2010/0298908 A1 | 11/2010 | Vardiman |

(56) References Cited

U.S. PATENT DOCUMENTS

| | | |
|---|---|---|
| 2010/0298917 A1 | 11/2010 | Vardiman |
| 2010/0298918 A1 | 11/2010 | Vardiman |
| 2010/0331807 A1 | 12/2010 | Whitehurst et al. |
| 2011/0071766 A1 | 3/2011 | Dolan et al. |
| 2011/0152988 A1 | 6/2011 | Whitehurst et al. |
| 2011/0154655 A1 | 6/2011 | Hetke et al. |
| 2011/0184495 A1 | 7/2011 | Wang et al. |
| 2011/0190860 A1 | 8/2011 | Harberts et al. |
| 2011/0208225 A1 | 8/2011 | Martens et al. |
| 2011/0213382 A1 | 9/2011 | Decre et al. |
| 2011/0218417 A1 | 9/2011 | Boogaard et al. |
| 2011/0224765 A1 | 9/2011 | Harberts et al. |
| 2011/0224766 A1 | 9/2011 | Tol et al. |
| 2012/0059444 A1 | 3/2012 | Pardoel et al. |
| 2012/0109262 A1 | 5/2012 | Martens |
| 2012/0109599 A1 | 5/2012 | Martens |
| 2012/0136420 A1 | 5/2012 | Pardoel et al. |
| 2012/0150256 A1 | 6/2012 | Martens |
| 2012/0184837 A1 | 7/2012 | Martens et al. |
| 2012/0277821 A1 | 11/2012 | Martens et al. |
| 2012/0303088 A1 | 11/2012 | Van Kaam et al. |
| 2012/0303089 A1 | 11/2012 | Martens et al. |
| 2012/0303107 A1 | 11/2012 | Decre et al. |
| 2013/0009691 A1 | 1/2013 | Blanken et al. |
| 2013/0172716 A1 | 7/2013 | Lozano et al. |
| 2013/0204318 A1 | 8/2013 | Young |
| 2013/0282090 A1 | 10/2013 | Decre et al. |

FOREIGN PATENT DOCUMENTS

| | | |
|---|---|---|
| EP | 0 892 654 | 1/1999 |
| EP | 0 895 483 | 2/1999 |
| EP | 0 959 942 | 12/1999 |
| EP | 1 048 319 | 11/2000 |
| EP | 1 102 607 | 5/2001 |
| EP | 1 257 320 | 11/2002 |
| EP | 1 446 189 | 8/2004 |
| EP | 1 514 576 | 3/2005 |
| EP | 1 750 798 | 2/2007 |
| EP | 1 890 764 | 2/2008 |
| EP | 1 931 419 | 6/2008 |
| EP | 1 985 579 | 10/2008 |
| EP | 1 993 665 | 11/2008 |
| EP | 2 046 441 | 4/2009 |
| EP | 2 066 396 B1 | 6/2009 |
| EP | 2 069 003 | 6/2009 |
| EP | 2 131 916 | 12/2009 |
| EP | 2 167 188 | 3/2010 |
| EP | 2 341 979 | 7/2011 |
| EP | 2 456 513 A1 | 5/2012 |
| EP | 2 542 303 A1 | 1/2013 |
| EP | 2 559 454 A1 | 2/2013 |
| EP | 2 620 179 A1 | 7/2013 |
| EP | 2 623 154 A1 | 8/2013 |
| EP | 2 626 108 A1 | 8/2013 |
| EP | 2 626 109 A1 | 8/2013 |
| EP | 2 626 110 A1 | 8/2013 |
| EP | 2 626 111 A1 | 8/2013 |
| EP | 2 656 875 A1 | 10/2013 |
| EP | 2 656 876 A1 | 10/2013 |
| EP | 2 674 193 A1 | 12/2013 |
| WO | WO-98/10010 | 3/1998 |
| WO | WO-03/022354 | 3/2003 |
| WO | WO-03/028521 | 4/2003 |
| WO | WO-03/066157 | 8/2003 |
| WO | WO-2004/045707 | 6/2004 |
| WO | WO-2005/002467 | 1/2005 |
| WO | WO-2005/112216 | 11/2005 |
| WO | WO-2006/104432 A1 | 10/2006 |
| WO | WO-2007/002144 | 1/2007 |
| WO | WO-2007/009070 | 1/2007 |
| WO | WO-2007/011611 | 1/2007 |
| WO | WO-2007/025356 | 3/2007 |
| WO | WO-2007/028003 A2 | 3/2007 |
| WO | WO-2007/042999 | 4/2007 |
| WO | WO-2007/092330 | 8/2007 |
| WO | WO-2007/100428 | 9/2007 |
| WO | WO-2007/108718 | 9/2007 |
| WO | WO-2008/003318 | 1/2008 |
| WO | WO-2008/005478 | 1/2008 |
| WO | WO-2008/016881 | 2/2008 |
| WO | WO-2008/035285 | 3/2008 |
| WO | WO-2008/035344 | 3/2008 |
| WO | WO-2008/051463 | 5/2008 |
| WO | WO-2008/064269 A2 | 5/2008 |
| WO | WO-2008/068759 | 6/2008 |
| WO | WO-2008/075294 | 6/2008 |
| WO | WO-2008/077440 | 7/2008 |
| WO | WO-2008/089726 | 7/2008 |
| WO | WO-2008/109298 | 9/2008 |
| WO | WO-2008/133616 | 11/2008 |
| WO | WO-2008/133683 | 11/2008 |
| WO | WO-2008/138305 | 11/2008 |
| WO | WO-2011/115999 | 9/2011 |

OTHER PUBLICATIONS

European Search Report for 13169272.5 dated Aug. 30, 2013.
European Search Report in 09803534.8 dated Jul. 21, 2011.
International Preliminary Report on Patentability for PCT/US2009/052077 dated Feb. 1, 2011.
International Search Report and Written Opinion in PCT/US09/52077 dated Sep. 25, 2009.
Rousche, et al., "Flexible polyimide-based intracortical electrode arrays with bioactive capability," IEEE Transactions on Biomedical Engineering 48(3): 361-371 (Mar. 2001).
Sepulveda et al., "Finite Element Analysis of Current Pathways with Implanted Electrodes", J. Biomed. Eng. 1983, vol. 5, pp. 41-48.

* cited by examiner

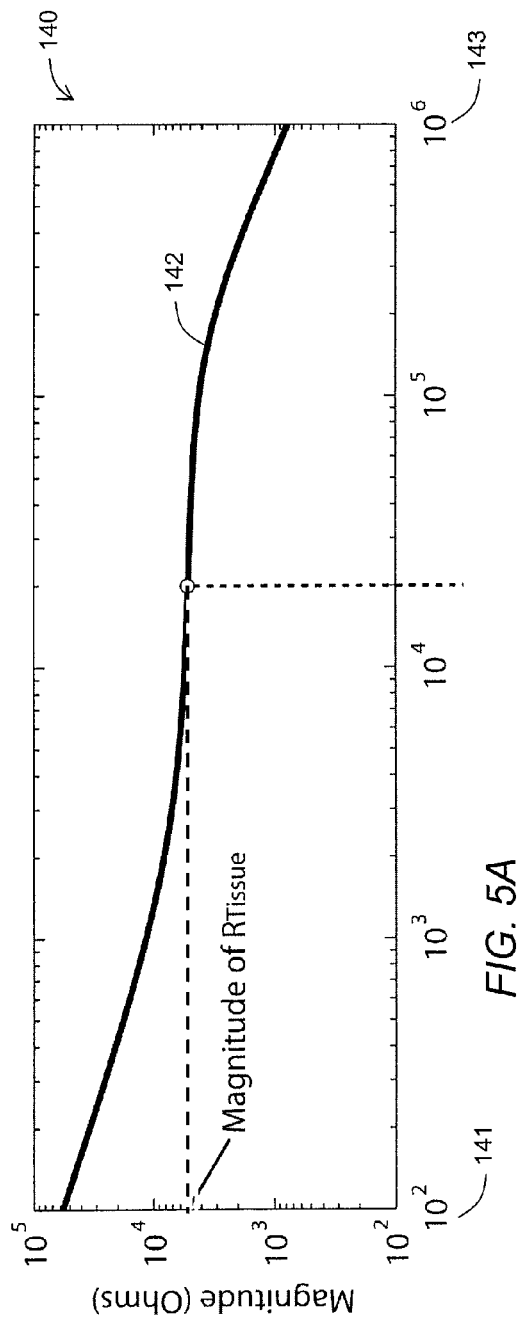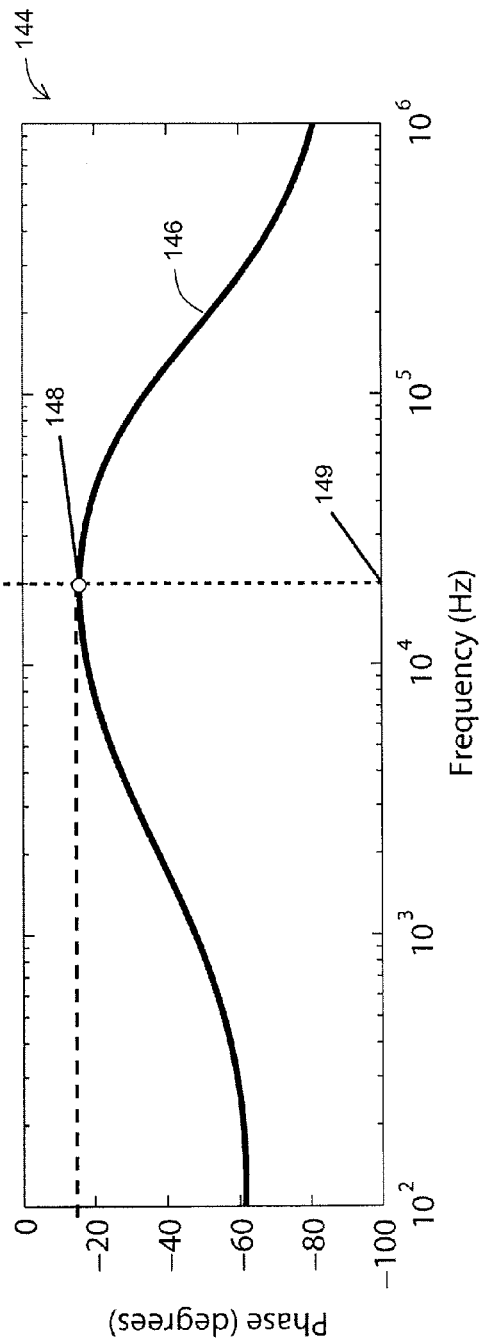
FIG. 5A
FIG. 5B

APPARATUS AND METHOD FOR OPTIMIZED STIMULATION OF A NEUROLOGICAL TARGET

RELATED APPLICATIONS

This is the U.S. National Stage of PCT International Application Number PCT/US2009/052077, filed Jul. 29, 2009, which claims priority to U.S. Provisional Application No. 61/084,870, filed Jul. 30, 2008. The contents of the foregoing applications are hereby incorporated herein in their entireties.

FIELD

The apparatus and method described herein relate generally to the use of conductive electrodes to stimulate tissue in a mammalian body. More specifically, the apparatus and method relate to use of conductive electrodes to stimulate a neurological target.

BACKGROUND

Neurostimulation is used effectively today to treat several diseases by placing electrodes in contact with neural tissue. Medical devices used in the course of neurostimulation generally transfer one or more of electric charge and electric fields to tissue, resulting in physiological change, which benefits the patient, or performs a physiological measurement. For example, electrical neurostimulation is used in the cochlea to produce responses similar to those produced from audible sounds. As another example, electrodes are placed near an animal's spine and configured to generate electrical pulses to treat pain. As another example, electrodes are placed in the deep brain for stimulation neurological targets including the subthalamic nucleus, the globus pallidus, configured to generate electrical pulses to treat the symptoms of movement disorders, such as Parkinson's disease, Essential Tremor or Dystonia. Such therapies may also treat the symptoms of Epilepsy and other neurological disorders. Neurostimulation is also used in other parts of the body, such as the retina, and the peripheral nervous system.

The localization of such electrical stimulation is important, and leads to higher efficiency in the therapy. Higher localization of the electrical stimulation generally requires smaller electrodes. The smaller electrodes exhibit particular electrical characteristics once placed into contact with an electrolyte such as the physiological fluid in the body.

The stimulation signals used in electrical stimulation can be fully described by their amplitude, pulse shape, and pulse frequency. Signal amplitudes are generally measured in units of voltage or current. Pulse shapes are generally described by their geometric shape and pulse width. For example, a commonly used pulse shape is a rectangular pulse with a pulse width, measured in units of time, such as micro-seconds. Finally, pulse repetition frequency generally describes the number of pulses per second applied to the electrodes. For example, a rectangular pulse of width 50 micro-seconds can be applied to an electrode at a frequency of 130 Hz. A suitable combination of amplitude, pulse shape, and pulse repetition frequency providing effective treatment is generally difficult to determine.

Several attempts to increase stimulation efficiency have been made. The methods used, however, have a direct effect on power consumption, tissue narcosis, and would potentially degrade the electrode materials due to corrosion. Empirical and simulation methods have been used to find a stimulation amplitude "threshold" at a particular frequency, such as 1 kHz or 10 kHz. Threshold determination techniques are explained by Palanker et al. and Jensen et al. empirically in the case of retinal stimulation.

The electrical stimulation of tissue with micro-scale electrodes presents several problems that have been previously identified, but have not been properly addressed. First, the interface impedance between a microelectrode and the surrounding tissue is extremely high, usually on the order of 1 MΩ for a 50 μm diameter electrode at biologically significant frequencies of 1 kHz. Such a high impedance leads to a high current requirement in order to achieve a sufficient voltage across the neural tissue for activation. Such high current can destroy the electrode material because it is susceptible to corrosion in the generally electrolytic environment of physiological fluid. Such corrosion would be undesirable as dangerous toxins can be released into the tissue. Furthermore, high currents will quickly decrease battery life for implantable devices.

SUMMARY

A system and method is described herein to identify a preferred frequency, and/or pulse shape, and/or amplitude, for electrical neuron stimulation. An electrical impedance is measured for at least one microelectrode positioned at a neurological target. The measurement is repeated across a span of different frequencies, with one of the measured electrical impedance values identified as being closest to a pure resistance. The measured frequency at which the identified impedance was obtained is referred to herein as a "peak resistance frequency." The parameters of a stimulation signal, i.e., the amplitude, pulse shape, and pulse frequency, can be determined and in some instances optimized using the characteristics of the peak resistance frequency. A signal having a substantial spectral content, energy, at or very close to the peak resistance frequency is subsequently applied to the at least one microelectrode to therapeutically stimulate tissue (neurons) at this frequency.

One embodiment of the invention relates to a process for stimulating a neurological target with at least one microelectrode with a preferred pulse shape. According to the process a respective electrical impedance value indicative of the microelectrode-tissue interface impedance is measured through each of several microelectrodes at each of several frequencies. A peak resistance frequency is identified from the electrical impedance values for each of the at least one microelectrodes. A preferred stimulation pulse shape is identified having a pulse width less than the inverse of the peak resistance frequency. In the case of a uni-polar pulse, such as a rectangular wave, the pulse width can be equal to half the inverse of the peak resistance frequency. The identified target can then be stimulated with the preferred pulse shape using a physiologically relevant pulse frequency which is not necessarily equal to the peak resistance frequency.

One embodiment of the invention relates to a device for stimulating a neurological target, including at least one microelectrode, an impedance analyzer, and a preferred-frequency detector. The impedance analyzer is in electrical communication with each of the at least one microelectrodes, which are, in turn, positionable at the neurological target. The impedance analyzer is configured to measure a respective electrical impedance value indicative of a microelectrode-tissue interface at each of a several different frequencies for each of the at least one microelectrodes. The preferred-frequency detector is in communication with the impedance analyzer and configured to detect from among the electrical impedance values measured at each of the at least one microelectrodes, a respective preferred frequency. In at least some embodiments, the preferred frequency is determined according to the measured impedance value having a minimum phase angle. The stimulation source is in communication with the at least one microelectrode and configured to stimulate the neurological target at the respective preferred frequency.

Another embodiment of the invention relates to a process for stimulating a neurological target with at least one microelectrode. According to the process, respective electrical impedance values indicative of the impedance of the microelectrode-tissue interface are measured through the at least one microelectrode, at each of several different frequencies. A preferred stimulation frequency is identified from the electrical impedance values, and the neurological target is stimulated at the preferred stimulation frequency.

Yet another embodiment of the invention relates to a process for stimulating a neurological target with at least one microelectrode. According to the process, respective electrical impedance values are measured through each of the at least one microelectrodes. The measured electrical impedance values are indicative of the microelectrode-tissue interface impedance at each of several different frequencies. A preferred stimulation frequency is identified for each of the at least one microelectrodes from the respective electrical impedance values. A preferred stimulation amplitude is identified at the preferred stimulation frequency for each of the at least one microelectrodes. The neurological target can then be stimulated at the preferred stimulation frequency and at the preferred stimulation amplitude.

Yet another embodiment of the invention relates to a process for stimulating a neurological target with at least one microelectrode. According to the process a respective electrical impedance value indicative of the microelectrode-tissue interface impedance is measured through each of several microelectrodes at each of several different frequencies. A peak resistance frequency is identified from the electrical impedance values for each of the at least one microelectrodes. A preferred stimulation pulse shape and amplitude are determined using the respective peak resistance frequency. The pulse shape is determined as described above, and its amplitude can be determined as inversely proportional to the impedance magnitude at the peak resistance frequency. The identified target can then be stimulated with the preferred pulse shape and amplitude, using either the peak resistance frequency, or a physiologically relevant pulse frequency.

Yet another embodiment of the invention relates to a process for stimulating a neurological target with at least one microelectrode. According to the process, a respective electrical impedance value indicative of the microelectrode-tissue interface impedance is measured through each of several microelectrodes at each of several different frequencies. A peak resistance frequency is identified from the electrical impedance values for each of a plurality of microelectrodes. One or more of the microelectrodes is identified from the respective peak resistance frequencies as being positioned at the neurological target.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 5A and FIG. 5B respectively illustrate magnitude and phase results obtained from an impedance spectroscopy sweep of an exemplary microelectrode-tissue interface obtained from microelectrodes of an implanted neurological target stimulator.

DETAILED DESCRIPTION OF THE PREFERRED EMBODIMENTS

The identification of the peak resistance frequency is a simple concept from impedance spectroscopy but is new to the field of neuronal stimulation at least because it has not yet been applied to microelectrodes. After implantation of microelectrodes at a target neurological site within a live animal, a tissue reaction progressively forms around the microelectrode array. The tissue reaction has been observed to change substantially within a period immediately following implantation, subsequently stabilizing after this initial period. This tissue reaction tends to alter electrical current flow for the individual microelectrodes, as their respective microenvironment varies. In general, the impedance of a respective microelectrode-tissue interface is substantially different for each microelectrode of an array of microelectrodes.

Using a technique referred to herein as electrical impedance spectroscopy, it is possible to identify a preferred frequency for each microelectrode at which the electrical impedance of the microelectrode is most resistive and least capacitive given the surrounding tissue. Stimulation of the neurological site performed at or near this frequency, promotes minimal signal distortion, and maximum charge transfer to the surrounding tissue. There will be minimal signal distortion, because the capacitive components of the microelectrode-tissue interface have a minimal effect on the signal components, and maximum charge transfer because the microelectrode-tissue interface is mostly resistive. In some embodiments, various aspects of a stimulation signal can be adjusted. If stimulation at this frequency is not physiologically effective, or if the stimulation source is not enabled to deliver such a frequency, attributes of the pulse, such as its shape, can be optimized instead. The pulse shape can be adapted to have substantial spectral content near or equal to the peak resistance frequency by filtering it, or by otherwise setting the pulse width equal to about half of the inverse of the peak resistance frequency. The resulting filtered signal will lead to reduced distortion, and enhanced charge transfer.

Figure 1:
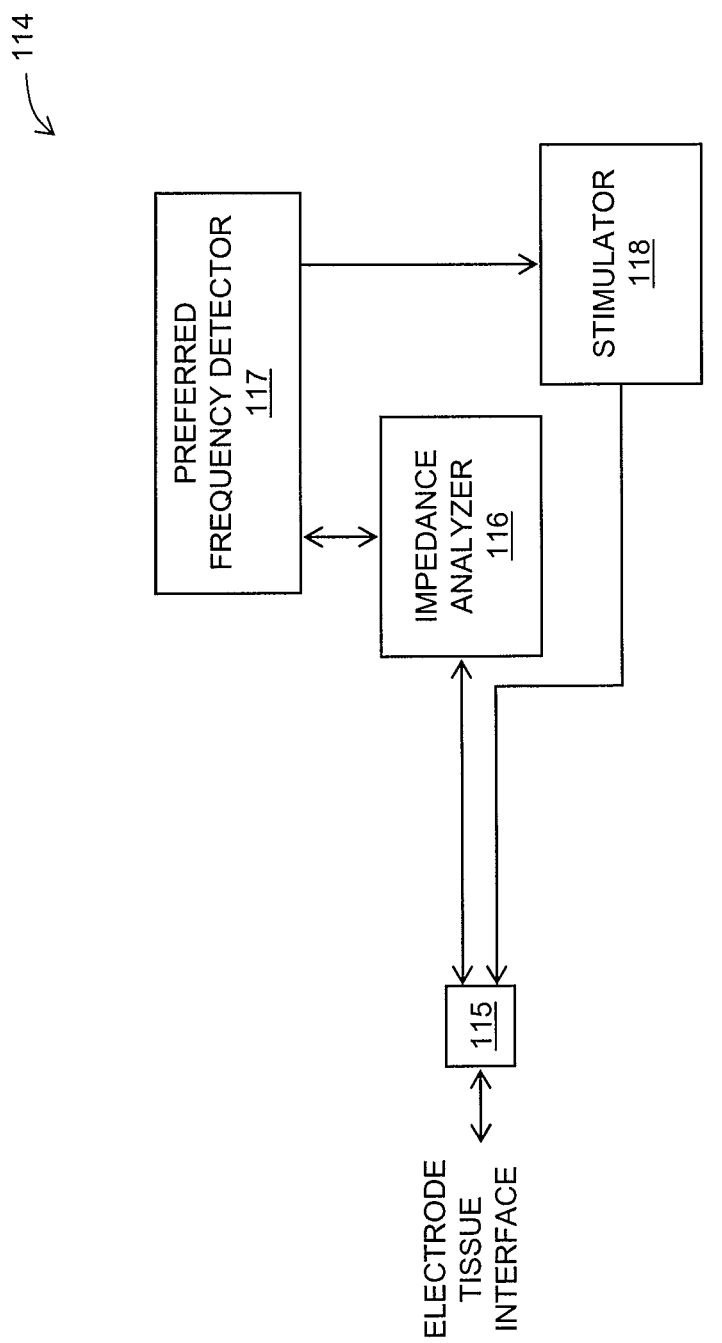
FIG. 1 is a functional block diagram of an exemplary embodiment of a neurological target stimulator.

Referring to FIG. 1, a functional block diagram of an exemplary embodiment of a neurological target stimulator 114 is shown. The stimulator 114 includes at least one microelectrode 115 positionable at a neurological target of interest. The stimulator 114 also includes an impedance analyzer 116 configured for measuring an electrical impedance, a preferred frequency detector 117, and a stimulator 118 for electrically stimulating the neurological target.

The impedance analyzer 116 can use any of various known techniques for measuring electrical impedance. Generally, the impedance analyzer 116 provides a test electrical signal having known or measurable attributes to the microelectrode-tissue interface. Such attributes include a voltage level of a voltage source, or a current level of a current source. The test voltage or current, as the case may be, when applied to the microelectrode-tissue interface, induces a sensed current or voltage according to physical properties of the microelectrode-tissue interface. The impedance analyzer 116 can form a ratio of the test signal to the sensed signal, yielding an impedance value according to Ohm's Law: Z=V/I. As the microelectrode-tissue impedance Z is a complex quantity, each of the test and sensed electrical signals is identified as having both a magnitude and a phase.

In operation, the impedance analyzer measures a complex impedance of the microelectrode-tissue interface surrounding the at least one microelectrode 115. The impedance analyzer repeats the measurements at multiple different frequencies, by varying frequency of the applied test electrical signal. Preferably, the multiple frequencies span a frequency range that includes biologically relevant frequencies. The preferred frequency detector 117 identifies the measured impedance being closest to a pure resistance. Such a determination can be accomplished by identifying the measured impedance value having a phase value closest to zero. For example, a measured impedance can be identified having minimum absolute value phase (i.e., $MIN|\angle Z|$). Such a determination can also be accomplished by identifying the measured impedance value having a minimum reactance (i.e., $MIN(Im\{Z\})$). The frequency at which the impedance determined to be closest to a pure resistance is identified as the peak resistance frequency. The stimulator 118 is then adjusted to provide a stimulation signal at a frequency, or frequency band, at or near the preferred stimulation frequency. Alternatively or in addition, if a physiologically relevant pulse frequency is known, the stimulator 118 is adjusted to provide a stimulation signal with a pulse shape that has substantial spectral content equal to or near the peak resistance frequency. This preferred pulse shape is then delivered at the pre-determined pulse repetition frequency. Alternatively, if a physiologically relevant pulse frequency is known, and the stimulator 118 provides a pre-determined pulse shape, the temporal characteristics of the pulse shape can be tuned so that a substantial spectral content is provided at or near the preferred stimulation frequency. For example, for a stimulator delivering a substantially rectangular pulse, the pulse width of the rectangular pulse would be tuned to be equal to half the inverse of the peak resistance frequency. This preferred pulse width is then delivered at the pre-determined pulse frequency. As another example, for a stimulator delivering a biphasic charge balanced square pulse, the pulse width of the stimulation pulse, whether leading or lagging, would be tuned to be equal to half the inverse of the peak resistance frequency. This preferred pulse width is then delivered at the pre-determined pulse frequency. The stimulation signal is then applied to the at least one microelectrode 115.

Figure 2:
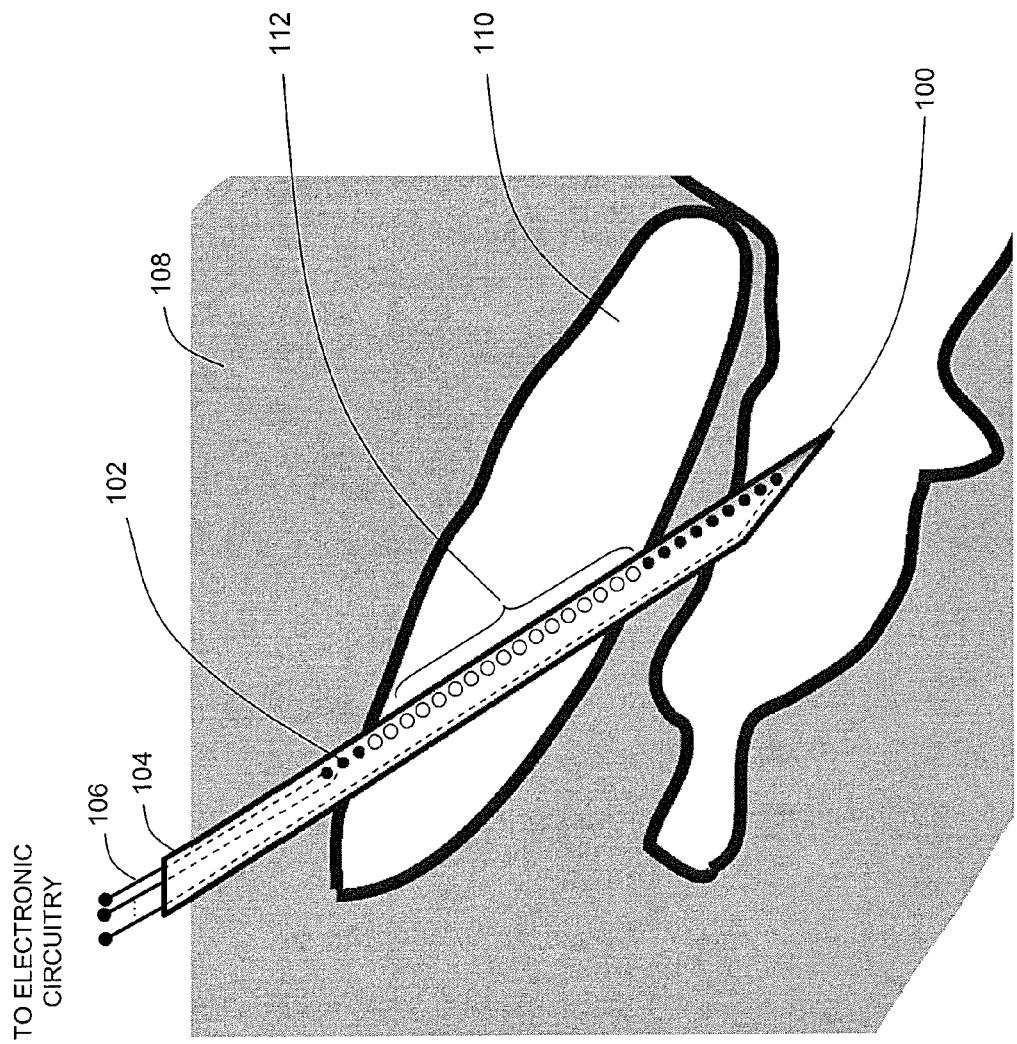
FIG. 2 is a cross-sectional view of a portion of an anatomy illustrating an exemplary microelectrode structure positioned at a neurological target.

Referring to FIG. 2, a cross-sectional view of a portion of an anatomy 108 is shown, illustrating an exemplary microelectrode probe 100 positioned at a neurological target 110. The probe 100 includes an array of microelectrodes 102 distributed along a supporting structure 104. Preferably, the probe 100 is shaped and sized to allow one or more of the microelectrodes 102 to be positioned adjacent the neurological target 110. To this end, materials used in construction of a probe, as well as construction features, size, and shape can be selected for biocompatibility. As illustrated, one or more microelectrodes 112 of the microelectrode probe are positioned in contact with the neurological target 110.

The supporting structure 104 can be a rigid, or semi-rigid structure, such as a polymeric cylinder. Alternatively or in addition, the structure can be a flexible structure, such as one or more flexible substantially non-conducting layers (i.e., a dielectric ribbon) onto which the microelectrodes 102 are formed as electrically conductive film layers. The one or more microelectrodes 102 are in communication with electronic circuitry (not shown) through one or more electrical leads 106 that can be routed through an internal lumen of a cylindrical supporting structure 103 and/or formed using elongated film layers along a flexible, ribbon-like supporting structure 104.

The microelectrodes can be placed in the brain generally for stimulation of the cortex and for deep brain stimulation of neurological targets including the subthalamic nucleus, the globus pallidus. The microelectrodes can also be placed in other parts of the body, such as the retina, the peripheral nervous system for neurostimulation of such portions of an animal anatomy. Although microelectrodes are discussed generally throughout the various embodiments, there is no intention to limit the upper or lower size of the microelectrodes. The devices and methods described herein are generally scalable, with an microelectrode size determined according to the intended application. For at least some of the neurological applications, microelectrodes are dimensioned sub-millimeter. In some embodiments, microelectrodes are dimensioned submicron. In some embodiments, the microelectrodes are formed as planer structures having a diameter of about 50 µm that are arranged in a linear array with center-to-center spacing of about 100 µm. The planer structures of the microelectrodes can have regular shapes, such as circles, ellipses, polygons, irregular shapes, or a combination of regular and irregular shapes.

This device is implantable near a neurological target, such as a target brain structure, using common neurosurgical techniques such as stereotaxy or endoscopy. The device might be inserted without support, or within a cannula, which has an inner dimension smaller than the outer dimension of the device. The cannula would then be retracted once the device is in position. Alternatively, the device can be inserted with or without support from a cannula, but with a central rigid rod of outer diameter smaller than the inner diameter of a lumen in the device. The rigid rod, or stylet, is retracted once the device is in position.

The operator can connect the microelectrodes to a recording unit that is configured to identify certain regions of the neurological target (e.g., the brain) according to their electrical activity. The microelectrodes used to record from the neurological target can be the same microelectrodes as those used to stimulate the target. Alternatively or in addition, the microelectrodes used to record from the neurological target can be separate microelectrodes from those used to stimulate the target. As microelectrodes destined for recording may differ in one or more of size, shape, number, and arrangement, from those microelectrodes destined for stimulation, using different microelectrodes.

The microelectrodes can be connected to a stimulation source through one or more interconnecting leads. In some embodiments, at least a portion of the stimulation source can be extracorporeal. Alternatively or in addition, the stimulation source can be fully implanted within the body. Any implanted elements of the stimulation source are fabricated and/or contained with a hermetically sealed biocompatible envelop. Such biocompatible packaging of signal sources is well known, for example, in the area of artificial pacemakers.

The stimulation source may be a controllable signal generator, producing a desired signal according to a prescribed input. For example, the signal generator may receive an input indicative of a desired output stimulation signal frequency. Such output stimulation signals can have a variety of waveforms, such as pulses, charge balanced pulses, sinusoidal, square-wave, triangular-wave, and combinations of these basic waveforms. In some embodiments, the stimulation source includes a pulse generator for applying signals to the microelectrode site. The signals from the pulse generator can be connected directly to the microelectrodes, or they can be preprocessed using electronics. In some embodiments, such preprocessing electronics are embedded within the implantable device. The preprocessing electronics can filter certain parts of the original signal in order to transmit only the frequency components of the original signal that are at or near the Peak Resistance Frequency of the microelectrode. For embodiments in which there are more microelectrodes than signals, the electronics can route the stimulation signals to preferred one or more of the microelectrodes.

Figure 3:
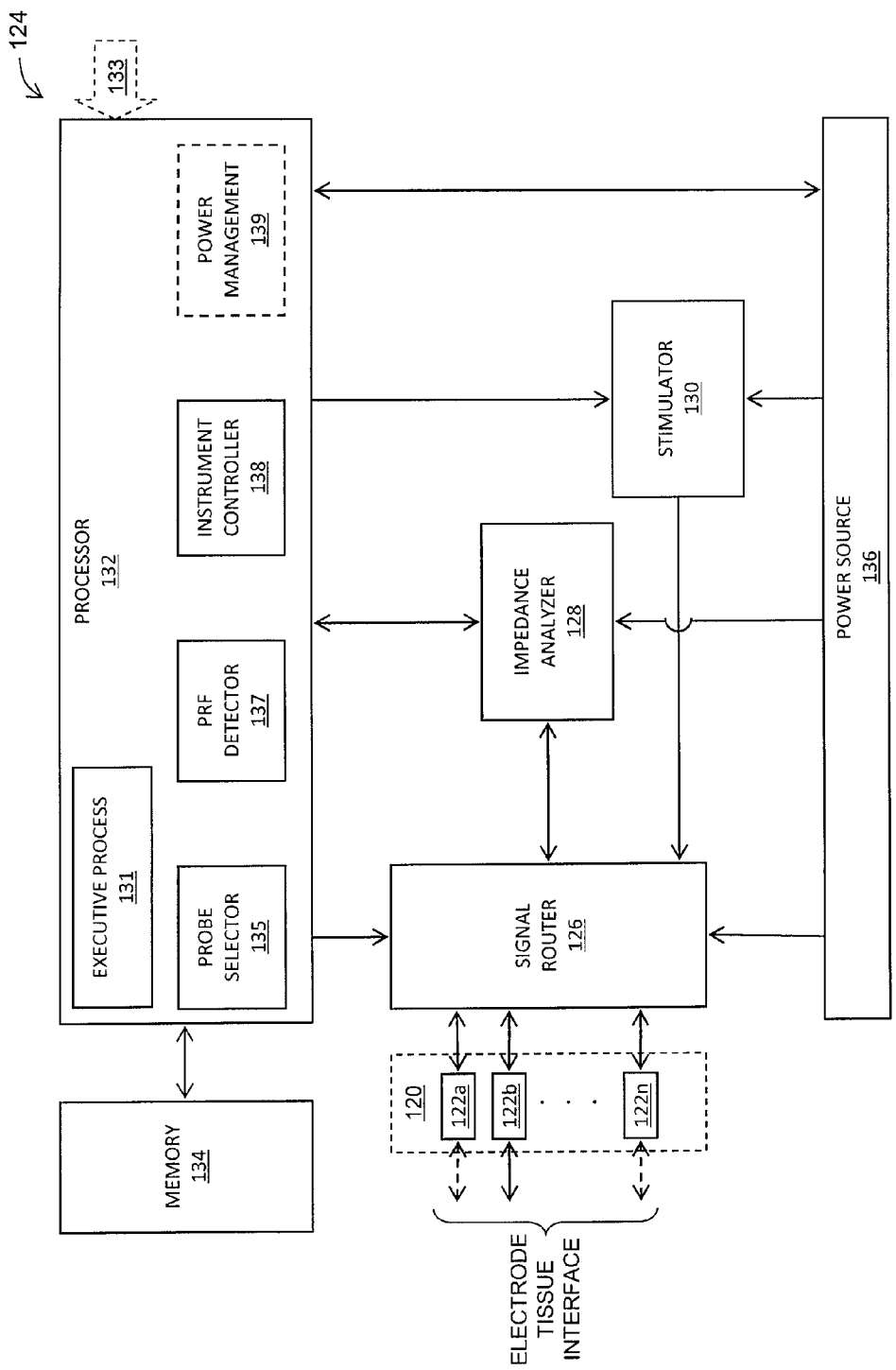
FIG. 3 is a functional block diagram of an exemplary alternative embodiment of a neurological target stimulator.

A more detailed functional block diagram of an exemplary embodiment of a neurological target stimulator 124 is shown in FIG. 3. The stimulator 124 includes a microelectrode array 120 having at least one microelectrode 122 positionable at a neurological target of interest. The stimulator 124 also includes an impedance analyzer 128 configured for measuring an electrical impedance and a stimulator 130 for electrically stimulating the neurological target. Each of the impedance analyzer 128 and the stimulator can be electrically coupled to one or more microelectrodes 122 of the microelectrode array 120.

In some embodiments, the stimulator 124 includes a signal router 126 as shown for selectively coupling one or more of the impedance analyzer 128 and the stimulator 130 to one or more microelectrodes 122. The signal router 126 can include a routing network for conveying electrical signals between one or more of the microelectrodes 122 and one or more of the impedance analyzer 128 and the stimulator 130. For example, the signal router 126 can include an electrically conductive branch circuit connecting each of the microelectrodes 122 to one or more of the impedance analyzer 128 and the stimulator. One or more switches can be included within such a conductive branch circuit for making or breaking a conductive path along the electrically conductive branch. Such switches allow for selective interconnection of one or more of the microelectrodes 122 to one or more of the impedance analyzer 128 and the stimulator 130. Such switches can be fabricated using one or more of micro-machined switches, such as micro-machined reed relays. Alternatively or in addition, one or more of the switches can be implemented using electronic switches, such as transistors.

The stimulator 124 also includes a processor 132 in communication with one or more of the impedance analyzer 128, the stimulator 130, and the signal router 126. The processor 132 can include one or more microprocessors, configured to control one or more of the impedance analyzer 128, the stimulator 130, and the signal router 126 according to pre-programmed instruction. The processor 132 can include an input/output port 133. Such a port 133 can be used to upload pre-programmed instruction, to obtain measured results, such as measured electrical impedance values, and to review settings of one or more of the impedance analyzer 128, the stimulator 130, and the signal router 126. The processor 132 can be in further communication with a memory 134 for storing one or more of pre-programmed instructions, measured results, and instrument settings.

The stimulator 124 can include one or more additional functional elements, such as a microelectrode selector 135, a peak resistance frequency detector 137, an instrument controller 138, and in some instance, a power manager 139 (shown in phantom). One or more of these additional functional elements 135, 137, 138, 139 can be implemented in hardware, firmware, software, or a combination of one or more of hardware, firmware, and software. In the exemplary embodiment, each of these additional functional elements 135, 137, 138, 139 is implemented as a processes running on the microprocessor 132. An executive process 131 can be provided to coordinate operation of the stimulator 124, including operation of the one or more additional functional elements 135, 137, 138, 139, when provided.

A memory 134, when provided, can be used to store, at least temporarily, measured impedance values for each of the at least one microelectrodes 122. Alternatively or in addition, the memory 134 can be used to store the peak resistance frequency determined for each of the at least one microelectrodes 122. The memory 134 can include one or more memory elements, such as random access memory (RAM), optical disk storage, magnetic disk storage, and flash memory. The memory 134 can be configured as a single element, or distributed, as in an on-chip processor memory and a separate memory chip.

The stimulator 124 also includes a power source 136 for providing power to one or more of the impedance analyzer 128, the stimulator 130, the signal router 126, and the processor 132. In some embodiments, the power source 136 is implantable within an animal body. Alternatively or in addition, at least a portion of the power source 136 can reside ex corporeal. The power source 136 can include an electrical storage element, such as a storage capacitor. Alternatively or in addition, the power source 136 can include an electrochemical storage element, such as a battery. Alternatively or in addition, the power source 136 can include an electromechanical power conversion element based on magnetic induction. The power source 136 can also include power conditioning circuitry configured to implement one or more of rectification, regulation, and filtration. In some embodiments, the power source is rechargeable.

Figure 4:
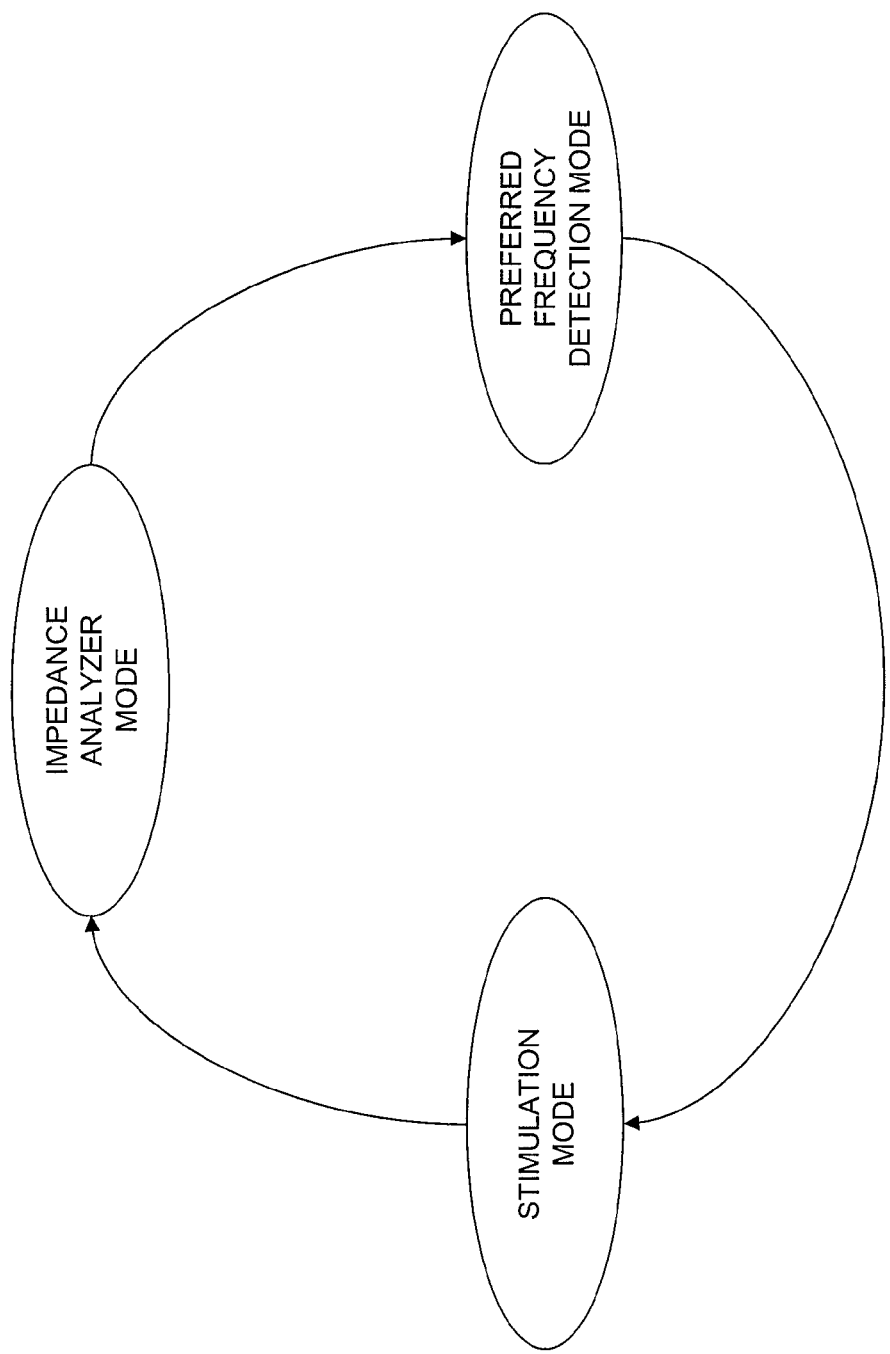
FIG. 4 is a schematic illustration of an exemplary embodiment of a state machine for controlling operational modes of a neurological stimulator.

In some embodiments, the processor 132 implements a state machine, such as the exemplary state machine illustrated in FIG. 4. The state machine can be used to select different operational modes of the stimulator 124 as described in reference to FIG. 3. For example, in a first mode or state, the stimulator 124 is configured to measure electrical impedance values through the microelectrode array 120. In this mode, the processor 132 enables the impedance analyzer 128 and the signal router 126 to place the impedance analyzer 128 in electrical communication with a selected one of the one or more microelectrodes 122. In a second mode or state, the stimulator 124 is configured to determine a peak resistance frequency for one or more of the microelectrodes 122 of the microelectrode array 120. In a third mode or state, the stimulator 124 is configured to stimulate the neurological target one or more of the microelectrodes 122 tuned to a respective peak resistance frequency, or stimulated with a preferred pulse shape as determined by the peak resistance frequency. In the third mode of the exemplary state machine, the processor disables the impedance analyzer 128 and enables the stimulator 130 prior to application of the stimulation signal.

Measured impedance results are provided in FIG. 5A illustrating the measured impedance magnitude 140 and FIG. 5B illustrating the measured impedance phase 144. In particular, magnitude and phase results obtained from an impedance spectroscopy sweep are illustrated of an exemplary microelectrode-tissue interface. The magnitude and phase together describe a phasor representing a complex impedance value—a ratio of a measured voltage phasor to a measured electric current phasor. Alternatively, the same complex electrical impedance can be portrayed differently, such as a combination of real (i.e., resistance) and imaginary (i.e., reactance) values. Alternatively or in addition, an admittance spectroscopy sweep can be obtained for the same microelectrode-tissue interface. The admittance is essentially an inverse of the impedance, with a real component reflecting a conductance, and an imaginary component reflecting a susceptance. A peak resistance frequency would be the frequency associated with the admittance being closest to a pure conductance. Although the illustrative embodiments are directed towards impedance, they are not intended to be limiting. Namely, the methods and devices described herein could be implemented to measure admittance without departing from the scope of the invention.

The electrical impedance spectroscopy sweep is performed for several sample frequencies distributed across a frequency range defined between a lower frequency limit 141 and an upper frequency limit 143. The frequency spacing between adjacent frequency samples can be constant (e.g., the frequency range divided by the number of samples−1), or vary according to frequency of the sample. In some embodiments, the frequency spacing between adjacent frequency samples is determined according to a common logarithm of the sample's frequency. The exemplary impedance spectroscopy sweep was performed at one microelectrode site between 100 Hz and 1 MHz. This sweep includes the neurologically relevant frequency range depending upon a selected neurological target. In some embodiments, a frequency range can be selected from about 100 Hz or less to about 10 kHz. In other embodiments, different frequency ranges are used that may extend above, below, or above and below this range. Alternatively or in addition, a selected frequency range may be narrower than the exemplary range provided herein. The magnitude of the measured impedance |Z| is illustrated on a log-log scale, varying between about 6 kΩ at 100 Hz and 800Ω at 1 MHz. The phase of the measured impedance ∠Z is illustrated across the same frequency span and ranges between about −80° and about −15°. The phase is negative, suggesting a capacitive reactance.

For the exemplary results measured, the minimum value of the magnitude of the phase angle (i.e., the phase angle closest to 0°) occurs at about 20 kHz. The absolute value of the phase angle increases at frequencies above and below 20 kHz. Thus, the impedance value at 20 kHz (i.e., |Z|=5 kΩ, ∠Z=−15° represents that impedance value of the measured values closest to a pure resistance, as it has the smallest reactance. The frequency at which this measurement occurs, referred to herein as the peak resistance frequency 149, is about 20 kHz. As each microelectrode site generally displays different characteristics, a different peak resistance frequency may be obtained for one or more of the microelectrodes.

Referring again to FIG. 3, the peak resistance frequency detector 137 receives measured impedance values from the impedance analyzer 128 (these values may be read from memory 134 when stored therein) and identifies from these values a peak resistance frequency associated with the measured impedance determined to be the closest to a pure resistor. The measured impedance value for each of the at least one microelectrodes 122 can be stored in memory 134 in a suitable data structure, such as a table, including at least the measured complex impedance phase angle and its associated frequency for each impedance spectroscopy sweep. A simple look up, or comparison operation can be performed on the stored data to identify the phase angle having a minimum absolute value. The frequency associated with this value would be the identified peak resistance frequency.

The executive process 131 initiates the stimulator 124 through the instrument controller 138 to provide a stimulation signal at or about the peak resistance frequency for the selected at least one microelectrode 122. By stimulating only at this frequency, or stimulating with a signal that has frequency components with bandwidth very close to this frequency, the optimized stimulation of tissue is achievable for the selected at least one microelectrode 122. The optimized stimulation of tissue generally allows for optimal transfer of electrical charge to the tissue, with minimal signal distortion. Each microelectrode site will generally display different characteristics, having a different peak resistance frequency.

Alternatively or in addition, the complex impedance can be used to set the threshold or signal amplitude level for stimulation applied by the stimulator. Such a preferred threshold or signal amplitude level can be selected as being most adapted to stimulate the surrounding tissue at that frequency. For example, if the tissue resistance at the Peak Resistance Frequency is found to be 20 kΩ, then the stimulator may adjust the stimulation signal amplitude in order to optimize the signal that is being transmitted to the tissue. For example, if the tissue resistance is relatively low, the stimulator may lower the stimulation amplitude in order conserve battery life or limit damage. If the tissue resistance is high, the stimulator may increase the stimulation amplitude in order to reach an appropriate threshold potential required for cellular stimulation. The relationship between the stimulation signal amplitude level and measured tissue resistance can be determined according to Ohm's Law. A greater applied current for the same tissue resistance will lead to an increased potential at the microelectrode-tissue interface.

Alternatively, or in addition, the complex impedance can be used to set the pulse shape applied by the stimulator. Such a preferred pulse shape can be selected as being the most adapted to stimulate the surrounding tissue, at a physiologically relevant pulse frequency. For example, if the peak resistance frequency is found to be 20 kHz, then the stimulator may adjust a predefined unipolar pulse shape, such as a square pulse, to have a pulse width, equal to one half the inverse of the peak resistance frequency. In this case, the pulse width would be adjusted to 25 micro-seconds. A square pulse with this pulse width would have a substantial spectral content at the Peak Resistance Frequency.

As another example, if the peak resistance frequency is found to be 20 kHz, then the stimulator may adjust a predefined bipolar pulse shape such as a sine wave, or charge balanced pulses, with a substantial spectral content at or near the peak resistance frequency. The optimized pulse shape generally allows for optimal transfer of electric charge to the tissue, with minimal signal distortion. Each microelectrode site will generally display different characteristics, having a different peak resistance frequency, and may therefore require different preferred pulse shapes.

Alternatively or in addition, the complex impedance can be used to filter the pulse shape applied by an existing stimulator. Such a preferred pulse shape can be selected as being the most adapted to stimulate the surrounding tissue, at a physiologically relevant pulse frequency, or at a frequency that the stimulator can deliver. For example, if the peak resistance frequency is found to be 20 kHz, then a filtering mechanism can be used to reshape a predefined pulse shape (e.g., a 100 microsecond wide pulse), such as a unipolar square pulse, to have a major spectral content at the Peak Resistance Frequency. Optimized pulse re-shaping generally allows for optimal transfer of electric charge to the tissue, with minimal signal distortion. Each microelectrode site will generally display different characteristics, having a different peak resistance frequency, and may therefore require different preferred pulse shapes. Although rectangular pulses are discussed in the exemplary embodiments, it is envisioned that other pulse shapes can be used, such as triangular, saw-tooth, trapezoidal, sinusoidal, raised cosine, and the like. In some embodiments, the shape of the pulse itself can be filtered, for example changing a rectangular pulse to a trapezoidal pulse.

Figure 6A:
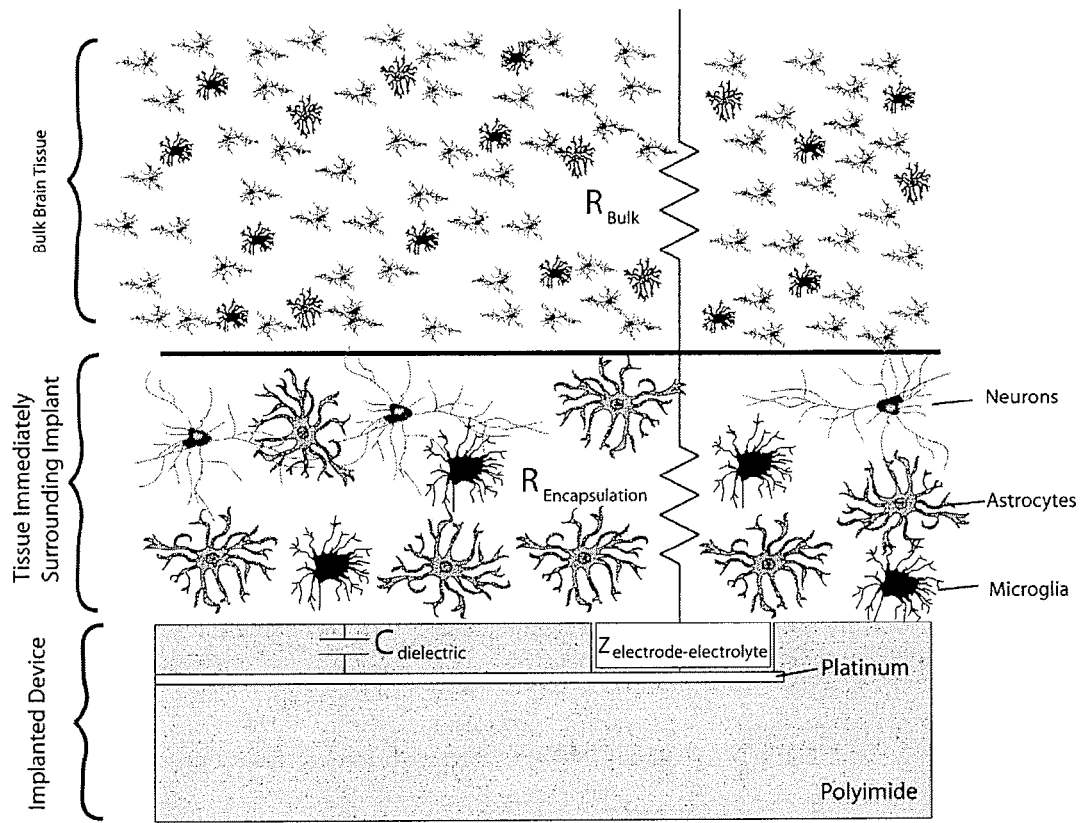
FIG. 6A is a cross-sectional view of a microelectrode-tissue interface for an exemplary microelectrode.

Referring to FIG. 6A, a cross-sectional view of an exemplary microelectrode-tissue interface is illustrated for a microelectrode implanted within brain tissue. Shown between the implanted device and the bulk brain tissue is an encapsulation layer immediately surrounding the implant.

Generally, biological tissue reacts in response to an implanted device, such as the neurostimulation prosthesis. The tissue reaction initiates immediately following implantation of the prosthesis and continues for an initial reaction period after which the tissue reaction may slow or substantially cease altogether. For the exemplary brain tissue-microelectrode interface, the tissue reaction has been observed to lead to an increase in astrocytes and microglia forming within the encapsulation layer over a period of about two weeks following implantation. As the electrical impedance of the microelectrode-tissue interface depends at least in part on the tissue immediately surrounding the microelectrode, such variations due to the changing encapsulation layer will result in corresponding variations to the measured impedance. Experimental results have indicated a reduction in the peak resistance frequency during this initial reaction period. The peak resistance frequency essentially stabilizes at that time. Understanding this variation, the impedance measurements can be repeated periodically, especially during this initial reaction period to adjust the stimulation frequency and thereby maintain efficient charge transfer throughout this period. After the initial reaction period, the impedance measurements can be performed periodically, but less frequently to track long term variations, and thereby maintain a proper peak resistance frequency.

Figure 6B:
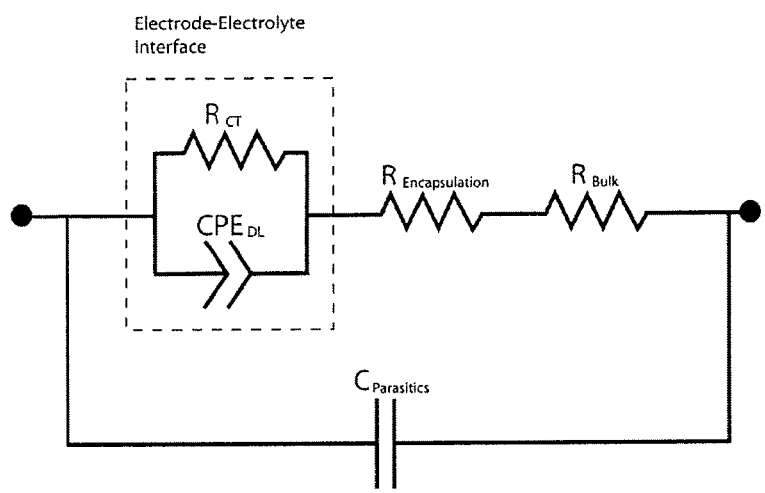
FIG. 6B is an exemplary circuit model approximating an impedance response of a microelectrode-tissue interface for an exemplary microelectrode.

An equivalent circuit model can be used to closely simulate the behavior of the electrode-tissue interface. FIG. 6B depicts an exemplary model of the interface. In an exemplary brain application, electrical impedance of the brain tissue can be split into two different resistances: (i) $R_{Bulk}$ representing a steady non-changing resistance, which describes tissue not immediately affected by implantation damage and tissue reaction, and (ii) $R_{Encapsulation}$ representing a resistance of the tissue immediately surrounding the implanted microelectrode, which increases as the tissue reaction due to implantation progresses. The term $R_{Tissue}$ may be used for brevity, in which $R_{Tissue} = R_{Bulk} R_{Encapsulation}$. The circuit element $R_{CT}$ represents a charge transfer resistance, shown in parallel with constant phase element $CPE_{DL}$ attributable to the double layer. The impedance of a CPE can be approximated by $$Z_{CPE} = \frac{1}{T(j\omega)^n}.$$

A constant phase element acts like a capacitor when the value n=1, and a resistor when the value n=0. The circuit element $C_{Parasitics}$ is formed between the metal traces and the electrolyte through the isolating material of the electrode. Other impedance components can be added to the model, such as a Warburg Impedance or the trace resistance. However, the circuit elements illustrated in FIG. 6B contribute to most of the impedance within the frequency range and voltage/current amplitude applicable for such brain tissue applications.

Using this model, a simulation can be performed by choosing values for the circuit model elements. A first exemplary model is simulated with parameters: $R_{CT}$=500 kΩ; $R_{Bulk}$=1 kΩ; $R_{Encapsulation}$=4 kΩ (therefore $R_{Tissue}$=5 kΩ); $CPE_{DL}$-T=100 nF; $CPE_{DL}$-n=0.8; and $C_{Parasitics}$=200 pF. The Peak Resistance Frequency is generally determined by finding the frequency at which the phase of the electrode-tissue impedance is closest to 0°. In this first exemplary model, the Peak Resistance Frequency is found at about 20 kHz as depicted in FIG. 5A and FIG. 5B.

The magnitude of the impedance is found to be about 5 kΩ at the Peak Resistance Frequency, but this was pre-determined by choosing $R_{Tissue}$=5 kΩ. When performing a measurement the algorithm to find Peak Resistance Frequency would give the frequency at which to determine the Impedance Magnitude of $R_{Tissue}$. This magnitude can be used to set the amplitude of the voltage or current used in stimulation. In this way, the preferred amplitude for stimulation at or near the Peak Resistance Frequency is determined.

Figure 5C:
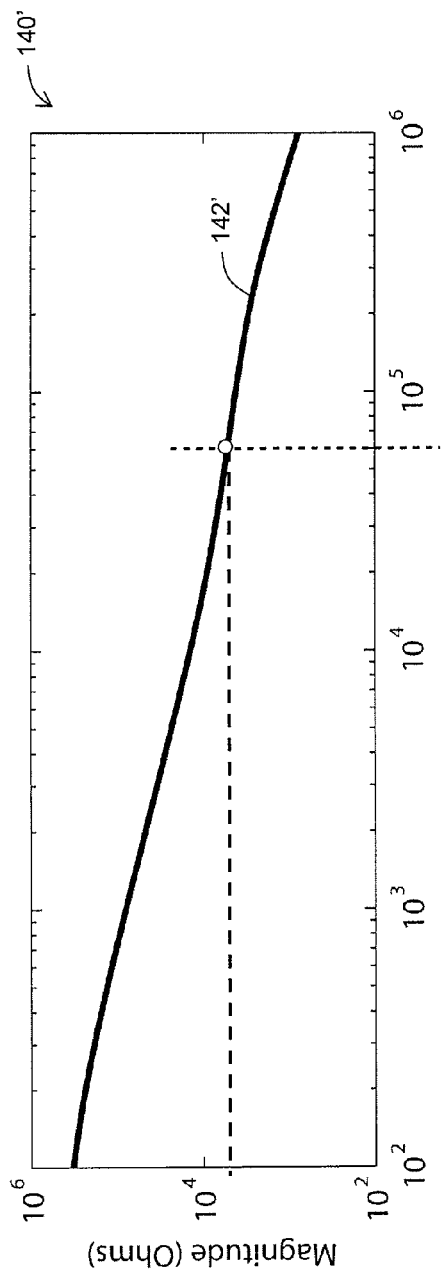
FIG. 5C and FIG. 5D respectively illustrate magnitude and phase results obtained from an impedance spectroscopy sweep of another exemplary microelectrode-tissue interface obtained from microelectrodes of an implanted neurological target stimulator.
Figure 5D:
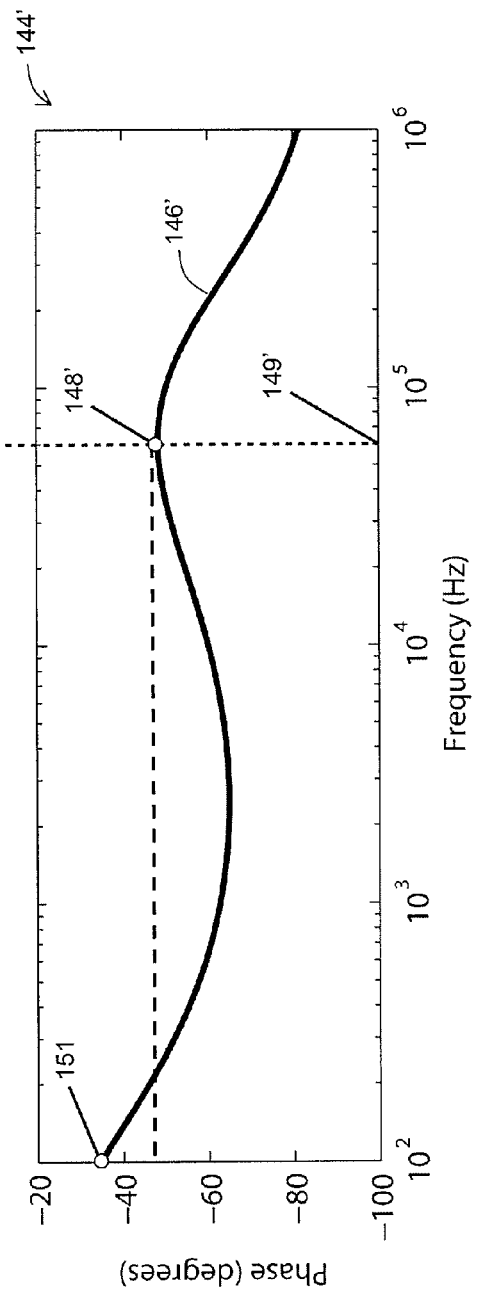

There may be instances in which the algorithm to identify the Peak Resistance Frequency is modified to avoid generating an incorrect result. Such a case is appropriate for applications in which the phase contribution of $R_{CT}$ may be closer to zero than the phase contribution of $R_{Tissue}$. Using the same equivalent circuit model as shown in FIG. 6B, a second exemplary simulation can be performed, also using the same parameters as the preceding exemplary model, but with $CPE_{DL}$-T=10 nF. This choice of parameter will make the impedance contribution from $R_{CT}$ more apparent over the frequency range being considered in the illustrative example, about 100 Hz to about 1 MHz. In this second exemplary model, without modification, the Peak Resistance Frequency would be found at 100 Hz as depicted in FIG. 5C and FIG. 5D. Although the impedance value at 100 Hz has a phase closest to zero, it represents an erroneous result, because it is not related to the tissue (i.e., $R_{Tissue}$). The signals delivered to the microelectrodes should be at or near the Peak Resistance Frequency due to $R_{Tissue}$, and not $R_{CT}$. In this instance the erroneous result can be avoided by noting that the phase at the correct Peak Resistance Frequency is the maximum of a peak in the phase.

Another method to avoid the erroneous result is to run the algorithm within a frequency range where it is known that the maximum would indeed only be contributed by $R_{Tissue}$. In this case, the frequency range for the algorithm that would provide the correct result would be 1 kHz to 1 MHz. Alternatively or in addition, relative peak resistive values of the impedance can be identified along the sweep, and selecting the relative peak having the highest frequency as the peak resistance frequency. In the illustrative example of FIG. 5A and FIG. 5B, two relative peaks would be identified: a first peak 151 at about 100 Hz and a second relative peak 148' at about 60 kHz. Selection of the higher frequency peak 148' provides a Peak Resistance Frequency.

Figure 7:
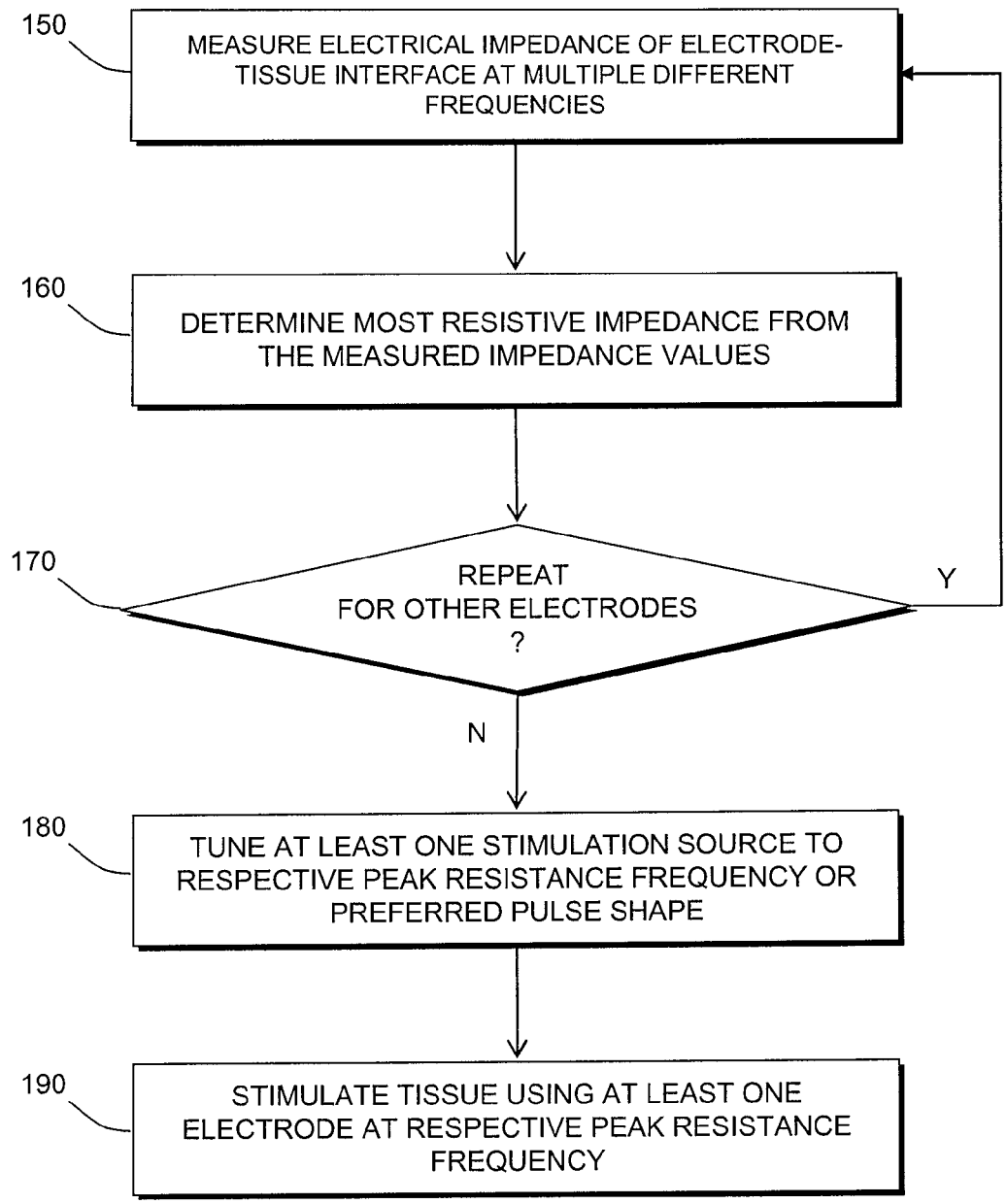
FIG. 7 is a flow diagram of an exemplary process for determining and stimulating a neurological target at a preferred stimulation frequency.

Referring to FIG. 7, a flow diagram of an exemplary process is illustrated for determining and stimulating a neurological target at a preferred stimulation frequency.

Operation.

As described in the flow diagram, the operation involves first measuring electrical impedance of microelectrode-tissue interface at multiple different frequencies (150) for a respective microelectrode site. An impedance analyzer circuit performs a frequency sweep and captures the impedance spectrum of the microelectrode-tissue interface. Such a measurement can be performed as a swept frequency measurement using standard impedance analyzer techniques. The most resistive impedance value is identified (160) from the impedance values measured at the respective microelectrode site. Measurement of the impedance and determination of the most resistive impedance can be repeated for other microelectrodes (170). Thus, such swept frequency measurements can be used to identify the optimum stimulation frequency, and/or optimum pulse shape, and/or optimum amplitude, for each microelectrode site. Thereafter, a stimulation signal is generated for at least one of the one or more microelectrode sites by tuning a stimulation source at, near, or about a peak resistance frequency or preferred pulse shape associated with the respective most resistive impedance (180). Alternatively, or in addition, the stimulation signal is generated with a preset, physiologically determined pulse frequency, e.g., a 100 microsecond wide pulse at a pulse repetition rate of about 130 pulses per second, having its pulse shape and/or amplitude tuned to an optimized value based on the peak resistance frequency characteristics. The signal can be generated by a circuit attached to the microelectrode site, or it can be filtered from an existing signal source, such as a pulse generator. The tuned stimulation signal can then be applied to a neurological target through a respective microelectrode (190) for optimal stimulation as described further herein.

Figure 8:
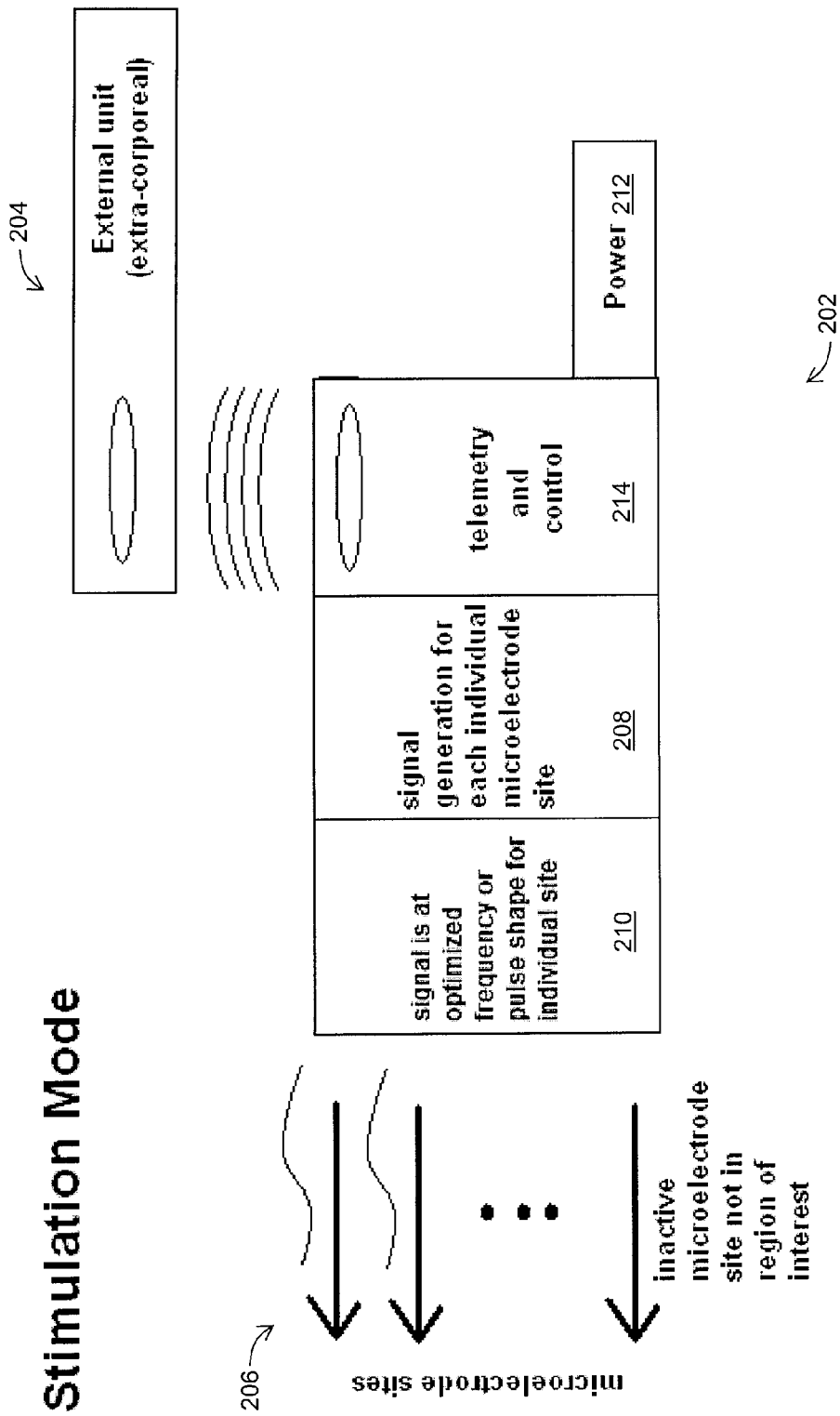
FIG. 8 is a functional block diagram of an exemplary embodiment of a neurological target stimulator configured in a stimulation mode.

Referring to FIG. 8, a functional block diagram of an exemplary embodiment of a neurological target stimulator 200 configured in a stimulation mode. The stimulator 200 includes an implantable portion 202 including a microelectrode array 206 positionable at a neurological target. The implantable portion 202 also includes a signal generation device 208 for actively stimulating the neurological target. In some embodiments, each of the one or more microelectrodes of the microelectrode array 206 is in communication with a dedicated signal generation device 208. In some embodiments, a signal filter 210 is provided to modify one or more attributes of a signal generator output, such as a signal amplitude, pulse shape, and/or pulse width. The respective stimulation signal is provided at an optimized frequency, pulse shape, or amplitude, for each individual microelectrode-tissue interface, based on a peak resistance frequency. The implantable portion 202 can include a power source 212, such as a battery. In some embodiments, the implantable portion 202 also includes a telemetry and control module 214 configured for external communication with an extra-corporeal unit 204. Such a feature can be used to provide extra-corporeal control for operating the implantable portion 202.

Figure 9:
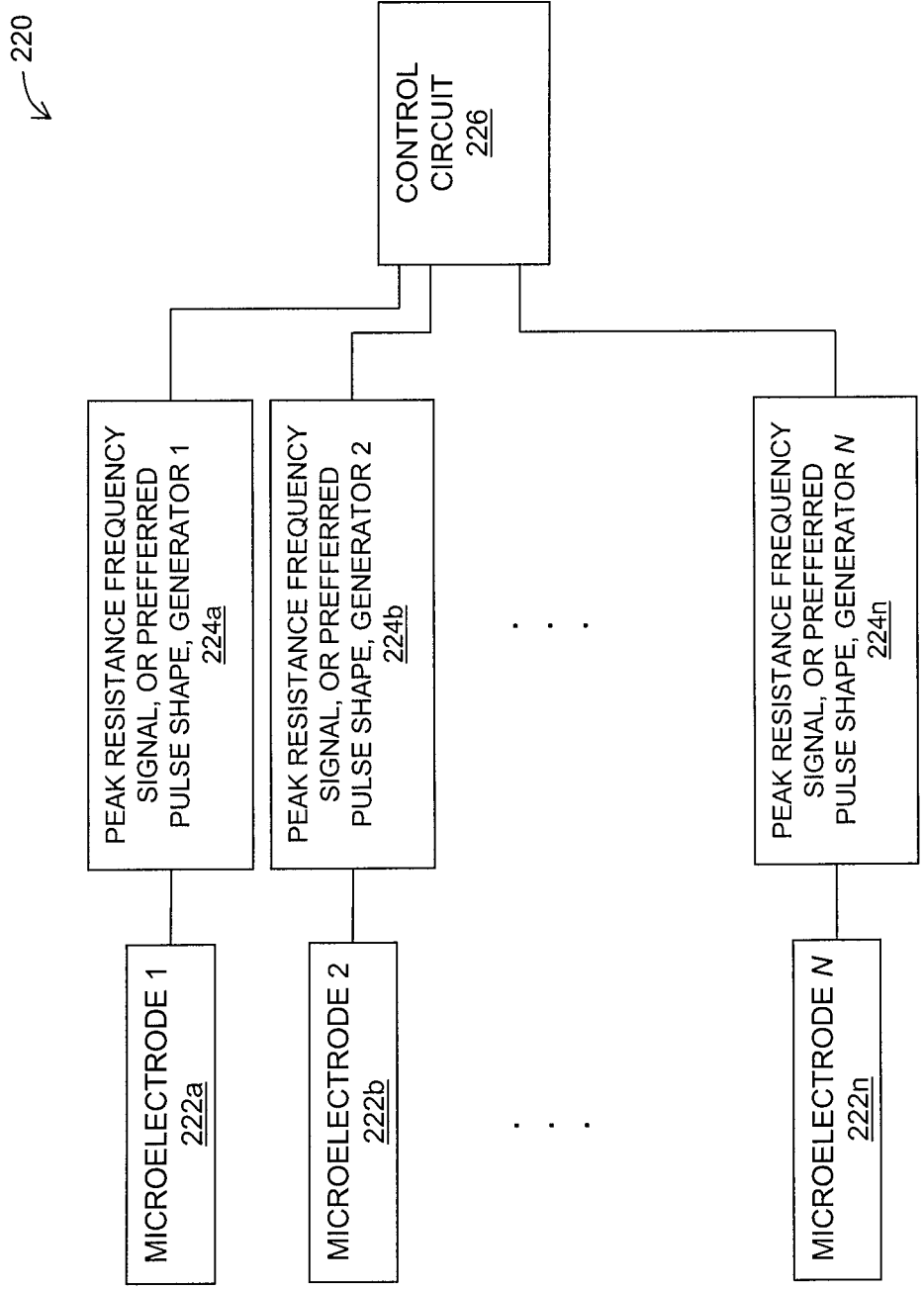
FIG. 9 is a functional block diagram of an exemplary embodiment of a neurological target stimulator having multiple tunable stimulation sources.

Referring to FIG. 9, a functional block diagram of an exemplary alternative embodiment of a neurological target stimulator 220 is illustrated configured in stimulation mode. The neurological target stimulator 220 includes multiple microelectrodes 222a, 222b, . . . 222n (generally 222). The stimulator 220 also includes a control circuit 226 in communication with each of the microelectrodes 222 through a respective signal generator 224a, 224b, . . . 224n configurable to provide a signal with characteristics based on the peak resistance frequency of the interconnected microelectrode site 222. The signal may be generated at or substantially near the peak resistance frequency. Alternatively, the signal may be generated with a pre-determined frequency, but its pulse shape is determined to have a spectral content equal to or near the peak resistance frequency. Alternatively, or in addition to, the amplitude of the signal can be adapted to the impedance magnitude at the peak resistance frequency.

Figure 10:
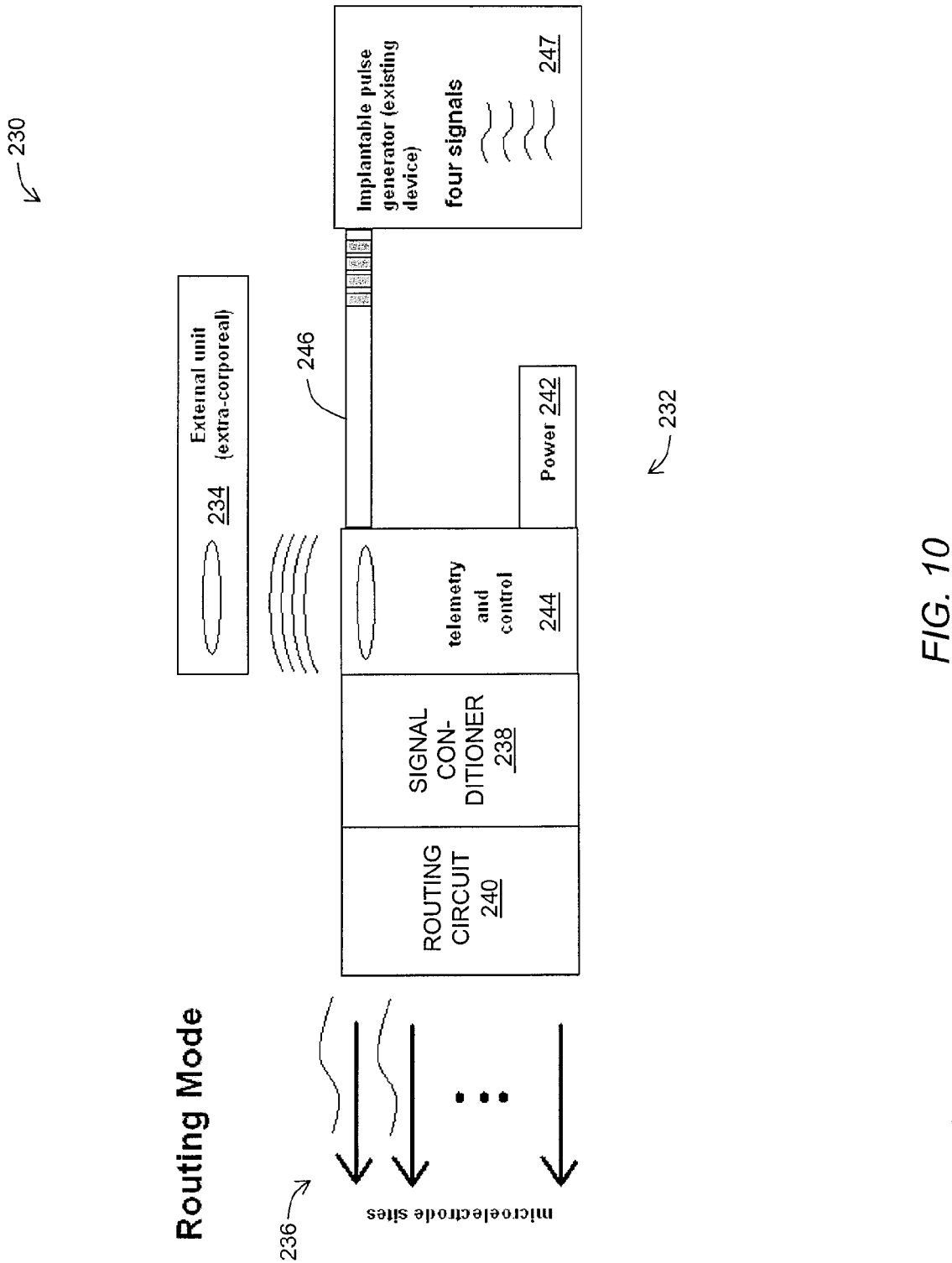
FIG. 10 is a functional block diagram of an exemplary embodiment of a neurological target stimulator configured for obtaining stimulation source signals from a pulse source.

Referring to FIG. 10, a functional block diagram of another exemplary embodiment of a neurological target stimulator 230 is illustrated configured in so-called routing mode. The stimulator 230 includes an implantable portion 232 including a microelectrode array 236 positionable at a neurological target. The implantable portion 232 also includes a signal routing circuit 240 configured to direct a stimulation signal to one or more of the microelectrodes 236 for actively stimulating the neurological target. In this embodiment, the stimulation signal is obtained from a separate, implantable pulse generator 247. The pulse generator 247 is in communication with the implantable portion 232 through an interconnection cable 246 containing one or more signal leads. The implantable portion 232 also includes at least one signal conditioner 238 configured to condition an output signal from the pulse generator 247 suitable for stimulation of the neurological target through one or more of the microelectrodes 236. The implantable portion 232 generally includes a power source 242, such as a battery. In some embodiments, the implantable portion 232 also includes a telemetry and control module 244 configured to communicate with an extra-corporeal unit 234, to provide controls for operating the implantable portion 232.

Filtering of an Existing Signal.

In some embodiments, the signal conditioner 238 includes a filtering circuit to pre-filter or gain adjust (e.g., pre-amplify and/or attenuate) or otherwise condition an existing signal before routing it to a microelectrode array. Several popular filter options include digital filters, such as infinite impulse response (IIR) filters, electronic filters using one or more electrical components, such as inductors and capacitors, and surface acoustic wave (SAW) devices. The filters can be designed through well known filter synthesis techniques to have a preferred performance features. Some of the controllable features in filter synthesis include filtration bandwidth, corner frequency, pass-band ripple, and relative sideband level. Such filters include categories referred to as Butterworth, Chebyshev 1 and 2, and Elliptic filters. The particular implementation—whether analog or digital, passive or active, makes little difference as the output from any implementation would still match the desired output. For an exemplary embodiment of a bandpass filter, the frequency response shown in FIG. 11A (magnitude) and FIG. 11B (phase) below, demonstrates a filter that would pre-filter a square wave signal in order to keep the most important elements of its frequency spectrum for a particular microelectrode site. The filter's center frequency (or pass band) Fc is selected at or near the peak resistance frequency of a respective microelectrode.

Figure 11:
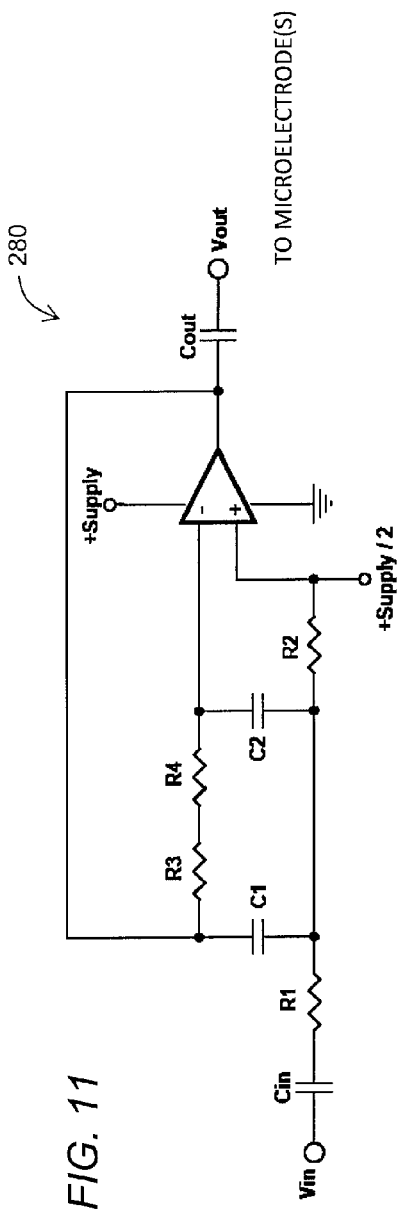
FIG. 11 is a schematic diagram of an exemplary embodiment of a bandpass filter positionable in electrical communication between a stimulation source and at least one microelectrode.
Figure 12:
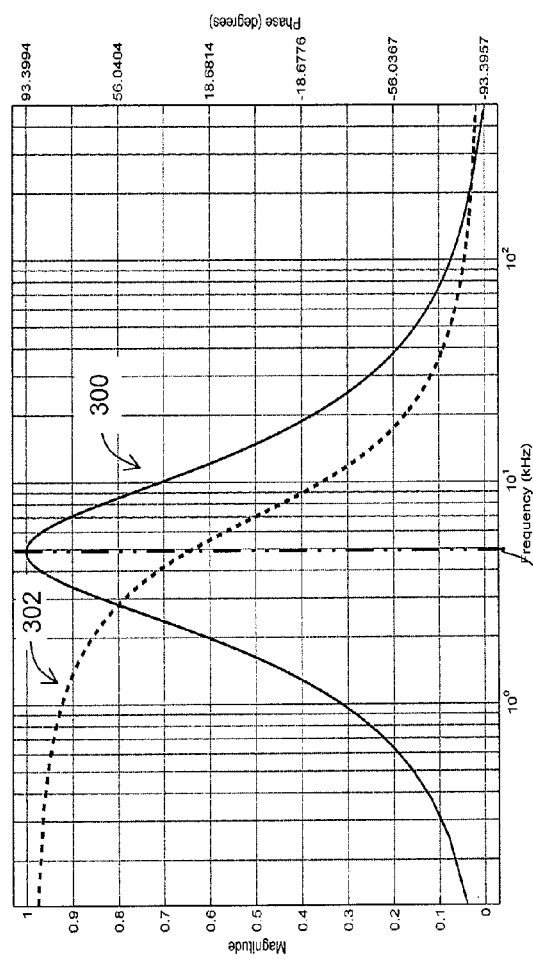
FIG. 12 illustrate a plot of representative performance curves for an exemplary bandpass filter implemented using a Butterworth design.

Referring to FIG. 11 a schematic diagram of an exemplary embodiment of an active bandpass filter is illustrated in electrical communication between a stimulation source and at least one microelectrode. The particular resistor R1, R2 and capacitor C1, C2 values are selected to synthesis performance of the active filter. Exemplary performance curves for the bandpass filter of FIG. 11 are illustrated in FIG. 12. The filter provides a pass band from about 600 kHz to about 1.8 MHz, with a substantially linear phase response within this band.

Figure 13A:
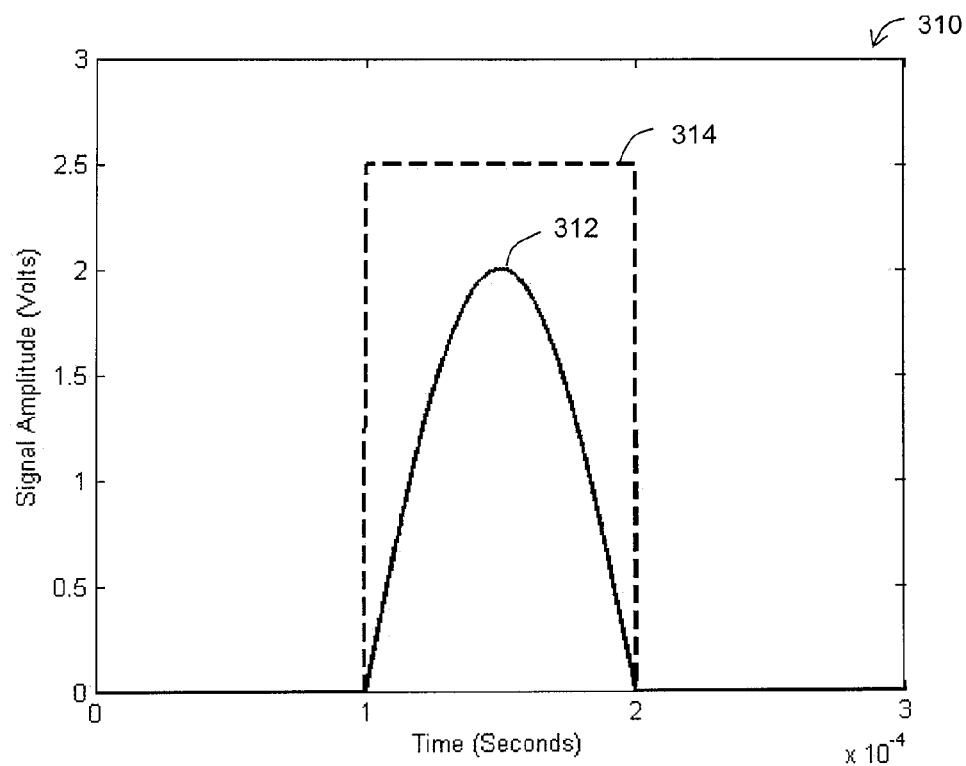
FIG. 13A illustrates plots of an exemplary pulse signal and an exemplary stimulation signal obtained therefrom after filtering.
Figure 13B:
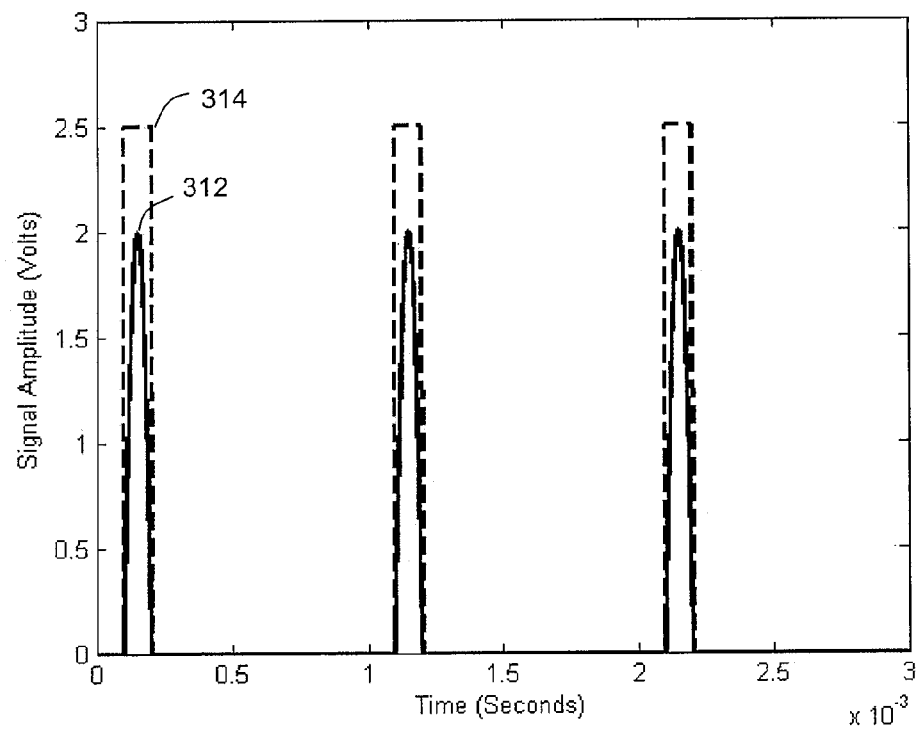
FIG. 13B illustrates a zoom-out of the filtered signal of FIG. 13A and a series of similarly filtered pulses.

An exemplary stimulation signal is illustrated in FIG. 13A, showing a representative square wave signal before and after filtering. The square wave signal (dashed) has an amplitude varying between +2.5 and 0, with a pulse width of about 100 µsecs. It is generally known that a square wave is a broadband signal. As described above, the square wave is filtered before being applied to a microelectrode site. The filtering process selects a portion of the frequency spectrum of the square wave, based on a desired output frequency. The solid signal 312 is a time-domain representation of the resulting filtered signal. FIG. 13B demonstrates how a pulse train of the exemplary filtered stimulation signals appears. The pulse frequency has been determined through physiological mechanisms. In this case the peak resistance frequency characteristics of the microelectrode site is used to shape the pulse only, and not the pulse frequency, thereby optimizing charge transfer and minimizing signal distortion. In some embodiments, the exemplary stimulation pulse may be of negative amplitude, in which case the filter would function in the equivalent manner and provide a negative output signal.

Figure 14:
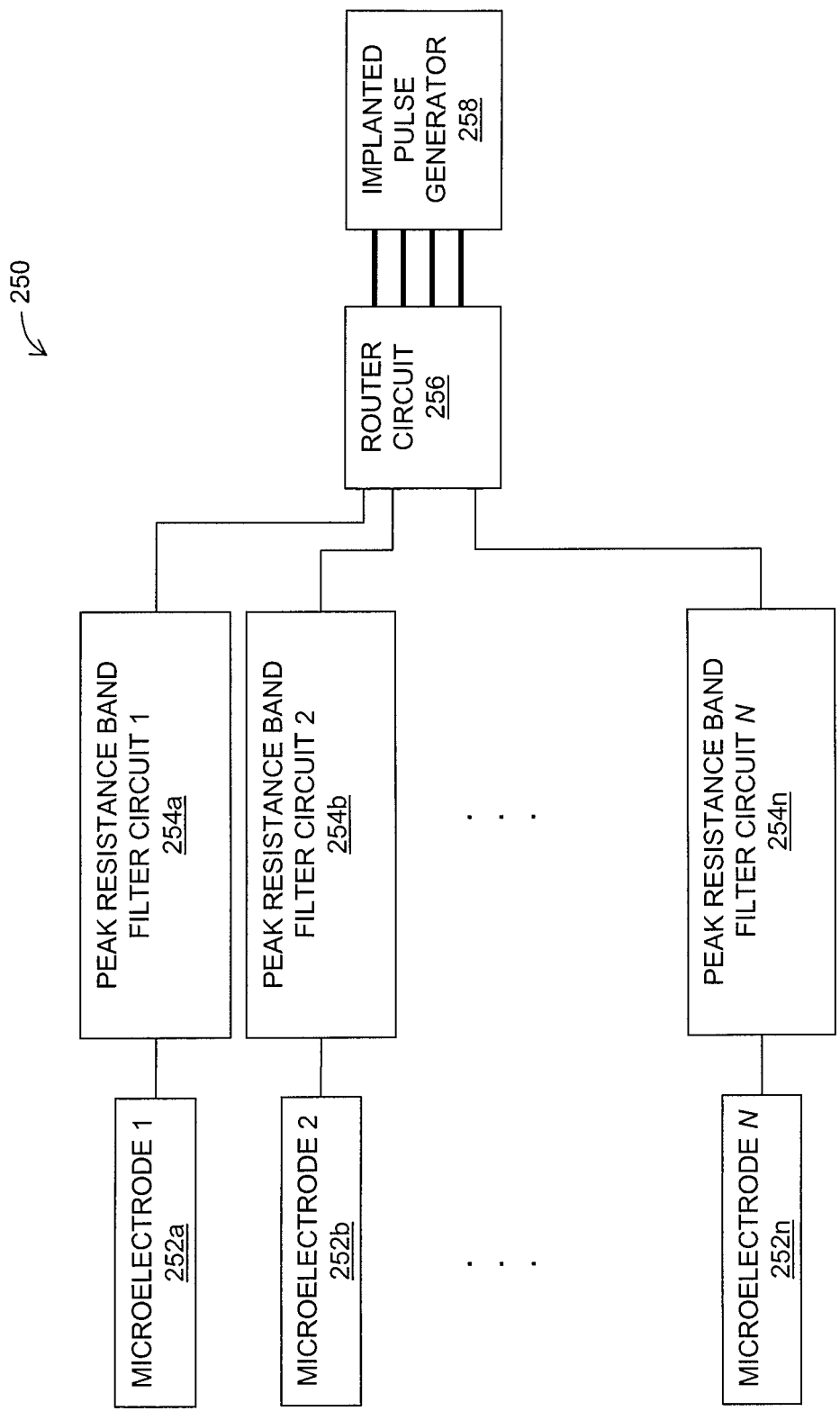
FIG. 14 is a functional block diagram of an exemplary embodiment of a neurological target stimulator configured for obtaining stimulation source signals from a pulse source.

Referring to FIG. 14, a functional block diagram of an exemplary alternative embodiment of a neurological target stimulator 250 is illustrated configured in stimulation mode. The neurological target stimulator 250 includes multiple microelectrodes 252a, 252b, . . . 252n (generally 222). The stimulator 250 also includes a router circuit 256 in communication with each of the microelectrodes 252 through a peak resistance frequency band filter circuit 254a, 254b, . . . 254n (generally 254). An implantable pulse generator 258 provides a pulse signal to the router circuit 256. The router circuit 256 directs the input pulse signal to one or more of the selected microelectrodes 252 through a respective peak resistance band filter circuit 254. The respective peak resistance band filter circuit 254 is tunable to a peak resistance frequency of the associated microelectrode 252, which may be determined using techniques described herein. The filter circuit 254 selects a sub-band of frequencies from the broadband input pulse signal that include the respective peak resistance frequency. The filtered signal is then applied to the neurological target through the respective microelectrode 252. In the case of such filtered pulses, the pulse repetition frequency is not necessarily equivalent to, or near the peak resistance frequency. The pulse frequency will be predetermined. The filter circuit therefore only reshapes the pulse shape, to consist of a major spectral content equal to or near the peak resistance frequency. Exemplary implantable pulse generators include the Medtronic SOLETRA™ neurostimulator, commercially available from Medtronic Corp, MN.

Figure 15:
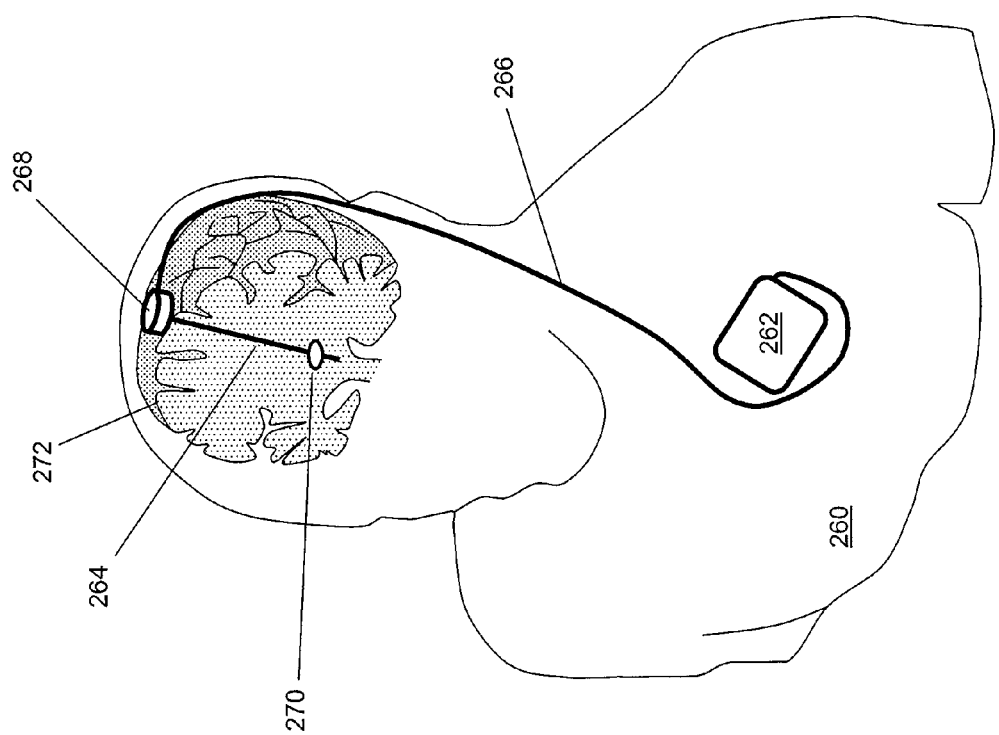
FIG. 15 is a perspective view of a portion of a human anatomy illustrating an exemplary neurological target stimulator implanted therein.

A perspective view of a portion of a human anatomy is illustrated in FIG. 15, showing implantation of an exemplary neurological target stimulator positioned for deep brain stimulation. A microelectrode probe 264 is positioned at a neurological target 270 within a human brain 272. A portion of the electronics 268 may be implanted external to the brain to minimize invasion into the brain and/or to facilitate wireless access thereto. Another portion of the electronics, such as a pulse generator 262, is implanted at a remote portion of the subject's body, such as within the chest cavity as shown. A cable 266 is also implanted within the subject's body, and configured to interconnect the pulse generator 262 to the electronics 268.

Figure 16:
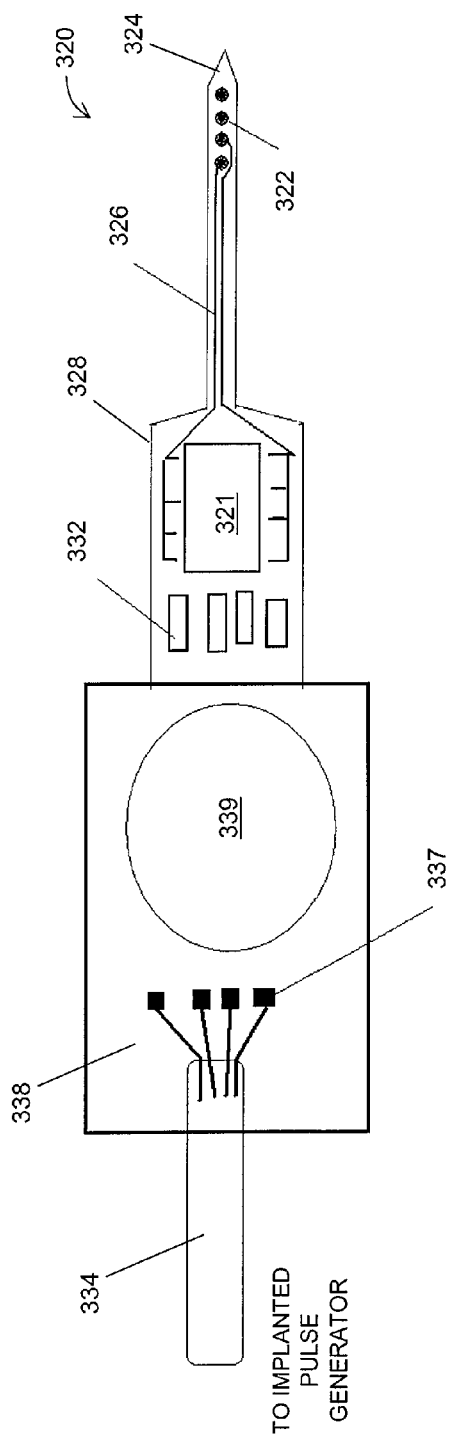
FIG. 16 is a top view of an exemplary embodiment of a neurological target stimulator.

A top view of an exemplary embodiment of a microelectrode assembly 320 is illustrated in FIG. 16. The assembly 320 includes an array of microelectrodes 322 positioned along a distal end of an elongated probe substrate 324. A first electronic assembly 328 is positioned at a proximal end of the elongated probe substrate 324. The first electronic assembly 328 can include one or more integrated circuit elements 321, such as a microprocessor, and one or more discrete electronic components 332. The first electronic assembly 328 is interconnected to each of the microelectrodes 322 through a respective trace 326 running along the elongated probe substrate 324. The electronic assembly 328 can be configured to implement one or more functions of the implantable neurological stimulator described herein. In some embodiments, the elongated probe substrate also includes at least a portion of the electronic assembly 328.

In some embodiments, the first electronic circuitry 328 is connected to an implanted pulse generator (not shown) through a cable 334. In some embodiments, as shown, a second electronics assembly (or a portion of the first electronics assembly) includes telemetry circuitry 339, such as a telemetry antenna. In the exemplary embodiment, at least a portion of electronic circuitry 328, 338 is positioned adjacent to the microelectrodes 322, for example being joined by the elongated probe substrate 324.

Mechanical Components.

The mechanical components and associated assembly processes serve to house the assembly 320 in a hermetic and biocompatible manner. They may also enable connection to an existing Implantable Pulse Generator or the extra-corporeal control unit. The extra-corporeal unit can provide power, programming ability, and retrieval of information. In some embodiments, the assembly 320 can be implanted much like currently available external cochlear stimulation systems. In an embodiment that includes an implantable pulse generator, it would serve to retrieve information and program the electrical unit to route the signals from the implantable pulse generator to the microelectrode array 322.

Microfabricated Components.

The device provides highly localized and efficient stimulation by incorporating microfabricated components, electronic components and mechanical components. The microfabricated component consists of a microelectrode array. This array can be implemented in a polymeric material such as polyimide, polyurethane, parylene, or polysiloxane (silicone) and includes thin film or plated layers of a metal or metal oxide with high charge transfer capability such as platinum, platinum-iridium, iridium, iridium oxide or titanium. The polymeric and metallic layers can be deposited sequentially and formed using established principles of microfabrication such as spin coating, DC/RF sputtering, photolithography, plasma etching, and etching with a mask consisting of a secondary or sacrificial material such as silicon dioxide or photosensitive resist. The metallic layer can be formed to create the microelectrode arrays and traces which connect the array to the electronics and housing. The polymeric layers serve to isolate the traces from each other but also provide the structure of the implant's stimulating/recording tip. There are several fabrication methods which can be described to build such a microfabricated component.

Electronic Components.

The electronic or microelectronic components of the device enable: (i) the ability to identify the peak resistance frequency for each individual microelectrode site using electrical impedance spectroscopy; (ii) stimulate at the characteristic peak resistance frequency of each microelectrode (this guarantees minimized signal distortion and maximum charge transfer to the tissue); or alternatively reshape the signal from an existing pulse generator to a preferred pulse shape; and (iii) stimulation and modulation of neuronal activity with the microelectrode array and the ability to select which microelectrode sites are stimulating.

The electronics can be implemented using discrete components, integrated circuit technology, digital signal processing (DSP), or a combination of all three. The electronics can be incorporated in one unit, or can be used in conjunction with an existing implantable pulse generator (IPG). The electronics may include a telemetric programming interface to properly condition or route the signal from the IPG to the microelectrode array.

Figure 17:
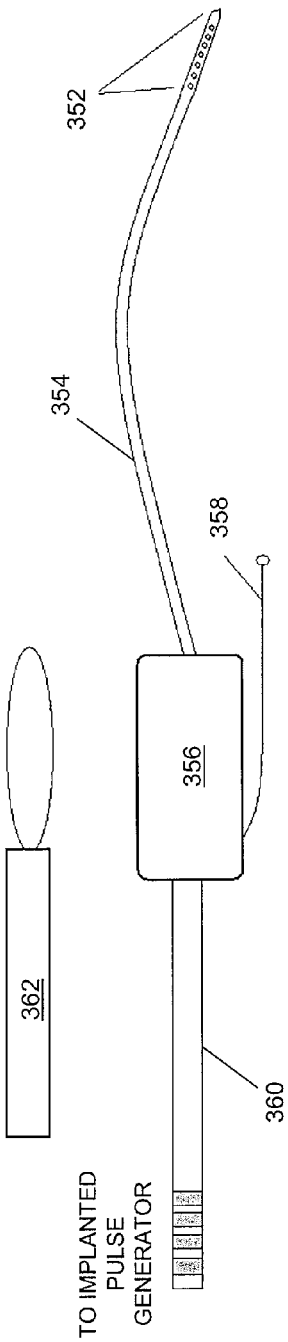
FIG. 17 is a top view of an exemplary alternative embodiment of a neurological target stimulator.

Referring to FIG. 17, a side view of an exemplary alternative embodiment of a microelectrode structure is illustrated. In this embodiment, an electronics assembly 356 is positioned remote from the microelectrode array 352. The microelectrode array 352 is joined to the electronics assembly 356 through an arrangement of interconnecting electrical leads 354. The electronics assembly 356 can be configured to implement one or more functions of the implantable neurological stimulator described herein. As illustrated, the electronics assembly 356 can also be connected to an implanted pulse generator (not shown) through an interconnecting cable 360. Alternatively or in addition, the electronics assembly 356 can include telemetry circuitry for communicating with an external telemetry device 362.

The electronics assembly can include an electrical grounding lead for interconnection to an electrical ground potential 358. In any of the embodiments described herein, impedance measurements and/or stimulation can be implemented between two or more microelectrodes (e.g., adjacent microelectrodes). Alternatively or in addition, impedance measurements and/or stimulation can be implemented between one or more microelectrodes and an electrical ground reference. Alternatively or in addition, impedance measurements and/or stimulation can be implemented between one or more microelectrodes and the casing of the implantable pulse generator.

Figure 18:
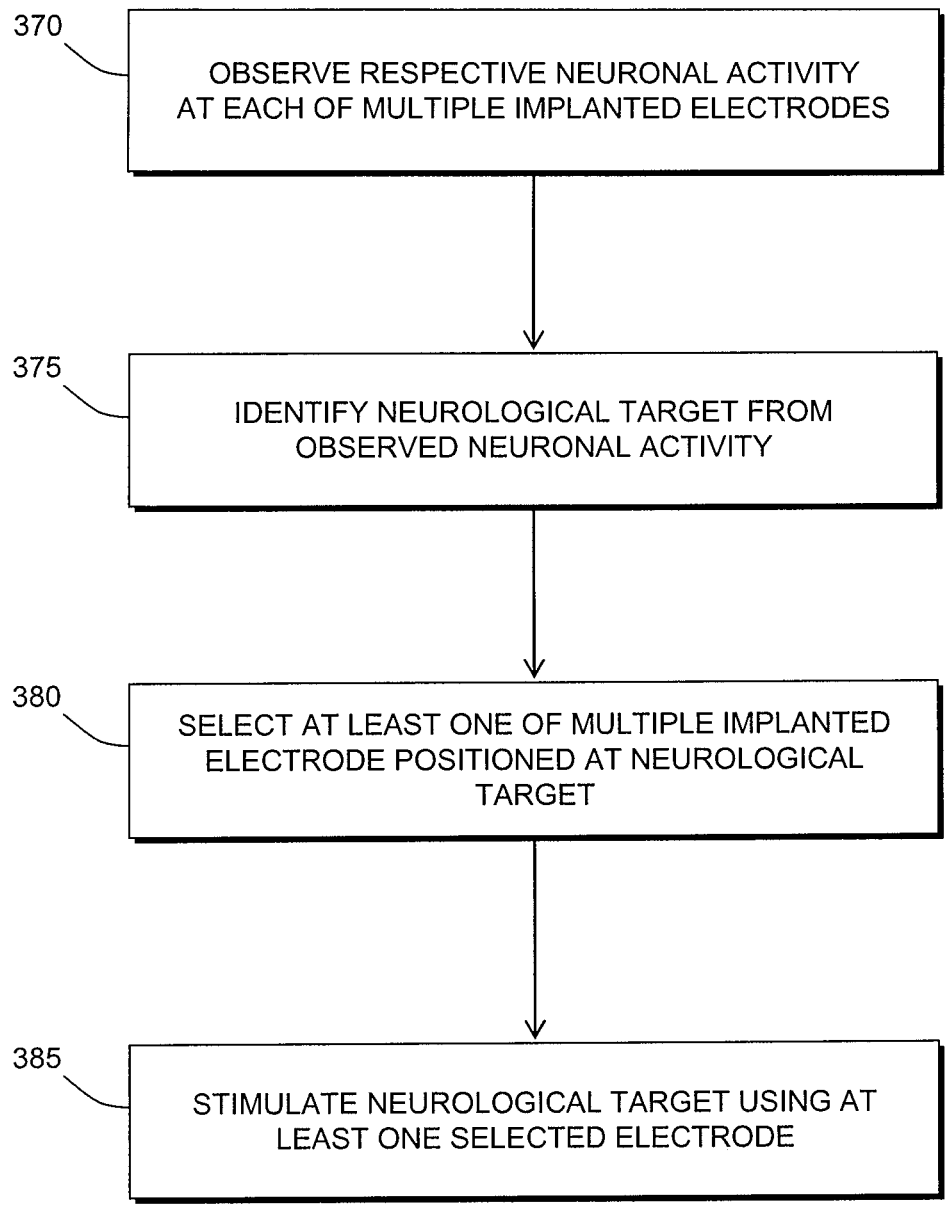
FIG. 18 is a flow diagram of an exemplary process for identifying implanted microelectrodes usable for stimulation of a neurological target.

FIG. 18 is a flow diagram of an exemplary process for identifying implanted microelectrodes usable for stimulation of a neurological target. Neurological target sites can be chosen as those sites determined to be actively stimulating. This can be accomplished by monitoring neuronal activity at a variety of different target sites, identifying those target sites having neuronal activity, and simulating the identified sites.

In more detail, a microelectrode array can be implanted within an animal body. The microelectrode array can be positioned at least partially within a neurological target area, the extent of the array spanning a region of the target. The array can take any of a number of various forms, such as linear, curvilinear, planar, conformal, and three-dimensional. Neuronal activity is measured at each microelectrode of the microelectrode array (370). A neurological target is identified at those microelectrodes at which neuronal activity above some threshold level (375). In some embodiments, the neuronal activity is recorded for subsequent analysis. At least one of the microelectrodes at which neuronal activity was observed are selected (380). The identified neurological target is subsequently stimulated using the at least one selected microelectrodes (385).

In some embodiments, the microelectrode selection process is run once subsequent to implantation. In other embodiments, the microelectrode selection process is repeated periodically to identify microelectrodes positioned at the target. As a neurological prosthesis may shift over time, the microelectrode array is designed to be of sufficient expanse to accommodate for any anticipated repositioning of the implant. The spacing between microelectrodes is selected to accommodate sufficient spatial resolution of the neurological target. In some embodiments, the microelectrode selection process is repeated regularly, as part of a course of treatment. That is to say, stimulation occurs responsive to measure neuronal activity.

Figure 19:
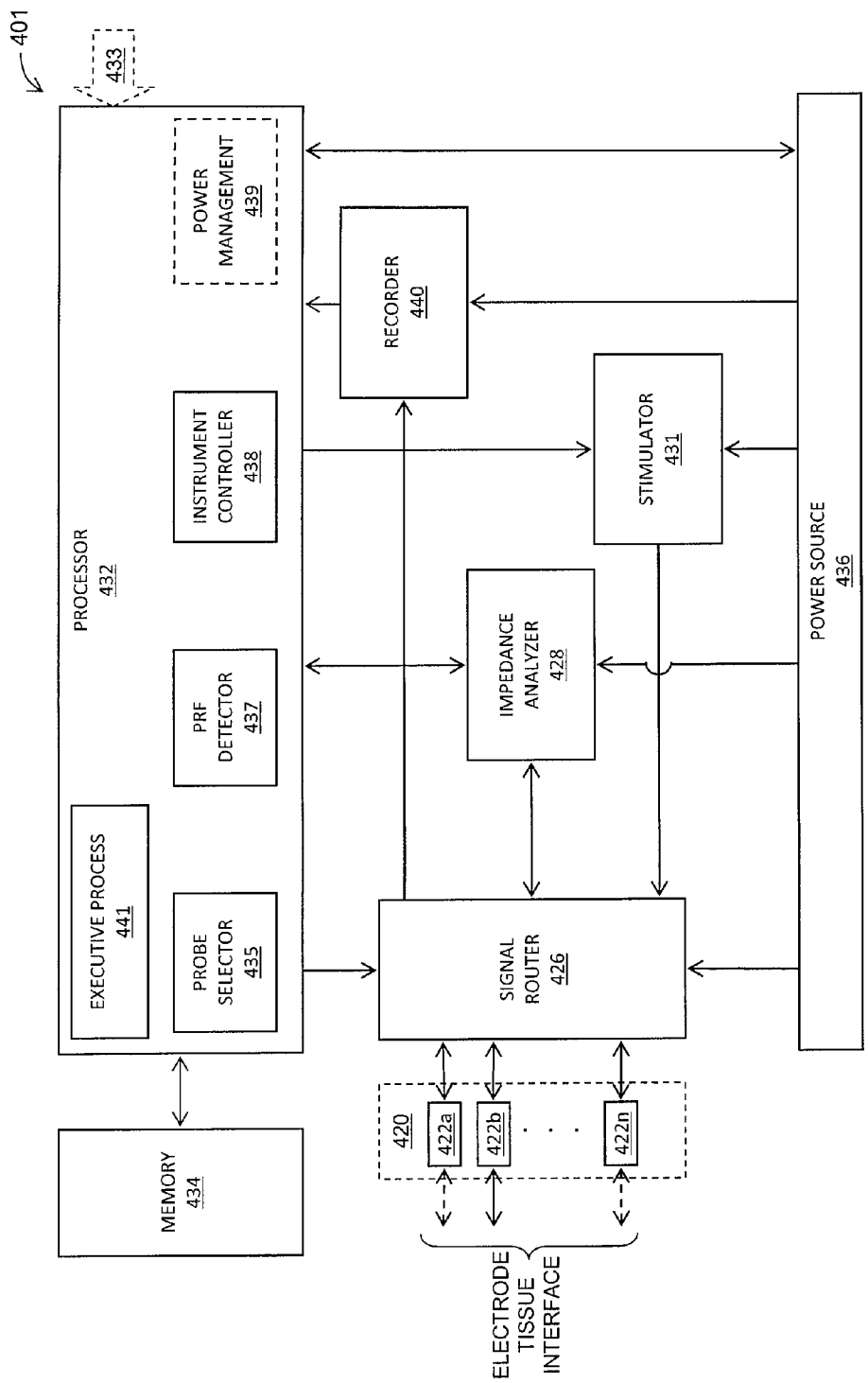
FIG. 19 is a functional block diagram of an exemplary alternative embodiment of a neurological target stimulator.

Referring to FIG. 19, a functional block diagram of an exemplary embodiment of a neurological target stimulator configured to observe neuronal activity and implement a microelectrode selection process, such as the exemplary process described in relation to FIG. 18. The exemplary neurological target stimulator 401 is essentially similar to the exemplary stimulator described in relation to FIG. 3, with the addition of a recorder 440. The sites that are actively stimulating are chosen as a result of the recording mode to simulate sites according to the presence or lack of neuronal activity at the site. In the exemplary embodiment, the recorder is coupled to one or more of the microelectrodes 422 through the signal router 426. The recorder 440 records neuronal activity at each of the interconnected microelectrodes. A microelectrode selection process 435 reviews the recorded neuronal activity, identifying those microelectrodes at which activity above a threshold value is observed. Identified microelectrodes can be stored in memory 434 and interconnected to other elements of the system, such as the impedance analyzer 428 and stimulator 431 through the signal router 426. Other functional elements, such as the peak resistance frequency detector 437, instrument controller 438, executive process 441, and power management 439 can operate as described herein.

Figure 20:
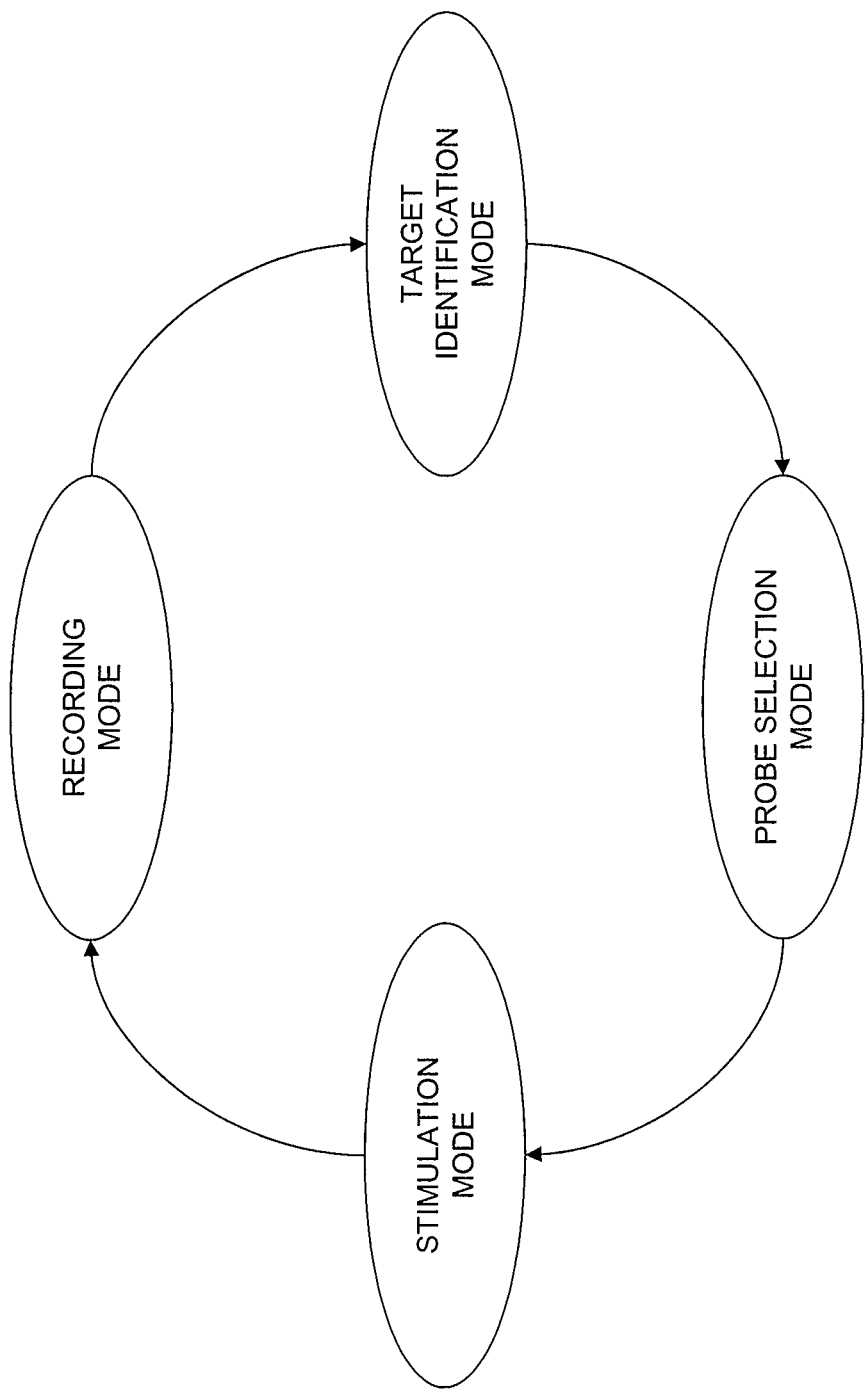
FIG. 20 is a schematic illustration of an exemplary embodiment of a state machine for controlling operational modes of a neurological stimulator.

In some embodiments, the processor 432 implements a state machine, such as the exemplary state machine illustrated in FIG. 20. The state machine can be used to select different operational modes of the stimulator 401 as described in reference to FIG. 19. For example, in a first mode or state, the stimulator 401 is configured to measure electrical neurological activity through the microelectrodes 422 of the microelectrode array 420. In this mode, the processor 432 enables the recorder 440 and the signal router 426 to place the recorder 440 in electrical communication with a selected one of the one or more microelectrodes 422. In a second mode or state, the stimulator 124 is configured to detect neurological activity indicative of the neurological target through one or more of the microelectrodes 422. The neurological activity may be measured in terms of an electrical potential, such as that produced by a synaptic potential of one or more neurons in the vicinity of the target. Generally, a measured response of the individual microelectrodes 422 will differ dependent upon their relative position with respect to the target. In a third mode, the probe selector 435 identifies one or more of the microelectrodes 422 positioned at or substantially near the intended target. The probe selector 435 in combination with the signal router 426 selects the identified microelectrodes 422. In a fourth mode or state, the stimulator 431 is configured to stimulate the neurological target using the one or more selected microelectrodes 422. The stimulation can be provided at a respective peak resistance frequency, or at an optimal pulse shape with respect to the peak resistance frequency, determined as described herein. In the fourth mode of the exemplary state machine, the processor 432 disables the impedance analyzer 428 and enables the stimulator 431 prior to application of the stimulation signal.

Figure 21:
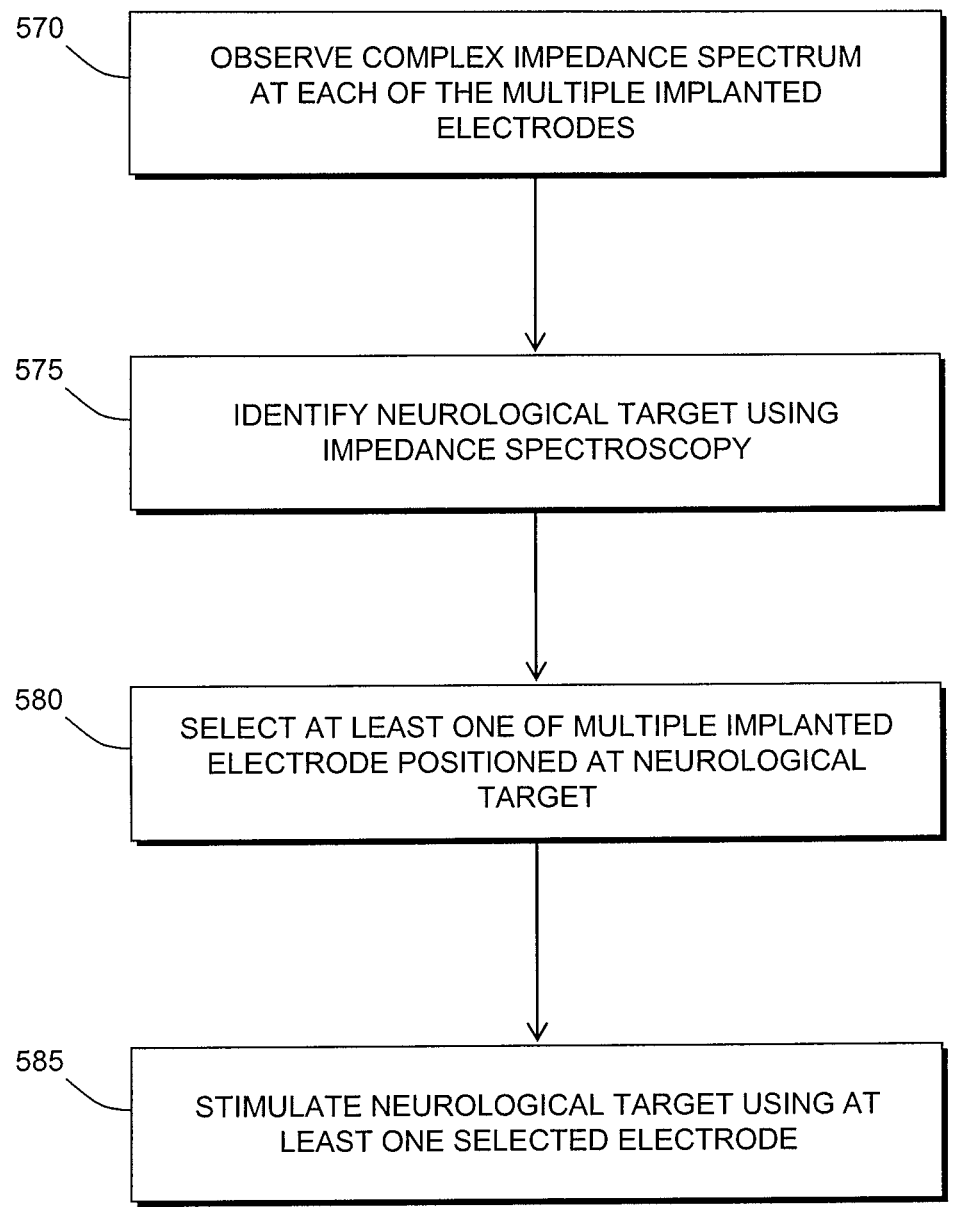
FIG. 21 is a flow diagram of an alternative exemplary process for identifying implanted microelectrodes usable for stimulation of a neurological target.

In some embodiments, the same frequency sweep as performed for finding the Peak Resistance Frequency can be used to identify anatomical targets and determine which microelectrodes are placed in contact with the target, and which microelectrodes are not. Thereafter the stimulation signals can be sent to the correct microelectrodes only. FIG. 21 is a flow diagram of an exemplary process for identifying implanted microelectrodes usable for stimulation of a neurological target using such a process. Neurological target sites can be chosen as those sites determined to be positioned at a neurological target by way of their peak resistance frequency. This can be accomplished by monitoring peak resistance frequency at a variety of different target sites, identifying those target sites having a relatively lower peak resistance frequency, and simulating the identified sites.

There are several differences between the anatomical areas of the brain that can be identified using impedance spectroscopy. For example distinction between grey and white matter can be identified according to a measured difference between each material's respective electrical conductance. Also, certain areas of the brain may induce a more substantial tissue response to an implanted probe, such as from glial cells, therefore creating a denser cellular sheath around the implant. The microelectrodes implanted in such an area of greater tissue reaction will register a lower Peak Resistance Frequency, a high impedance magnitude at the frequency, or both. If the target area is known to have a greater tissue response, then the microelectrodes in the correct area can be suitably identified and programmed to stimulate the target tissue. Likewise, if the targeted are is known to have a lesser tissue reaction than the surrounding region, then the microelectrodes in this area will have a higher Peak Resistance Frequency, a lower Impedance Magnitude at that frequency, or both. Therefore, the microelectrodes in contact with the targeted tissue can be similarly identified and programmed to stimulate the target tissue.

In more detail referring to FIG. 21, a microelectrode array can be implanted within an animal body. The microelectrode array can be positioned at least partially within a neurological target area, the extent of the array spanning a region of the target as described above (e.g., in relation to FIG. 18). Peak resistance frequency is measured at each microelectrode of the microelectrode array (570). Such measurements can be accomplished by any of the techniques described herein. A neurological target is identified using impedance spectroscopy at those microelectrodes for which a peak resistance frequency is measured below some threshold level (575). Microelectrodes lying outside of the target will not demonstrate a peak resistance frequency at this threshold level. The difference in peak resistance frequency in different neurological areas may be attributed to one or more of the difference in the extent of the tissue reaction in the different neurological areas, or the difference in electrical tissue properties of the different neurological areas. At least one of the microelectrodes, which is determined to be in the neurological target area is selected (580). The identified neurological target is subsequently stimulated using the at least one selected microelectrodes (585).

Any of the devices and methods described herein can be used to treat symptoms of movement disorders, such as Parkinson's disease, Essential Tremor or Dystonia. In the case of stimulating the hippocampus, such therapy can treat symptoms of Epilepsy. the devices and methods described herein can also be used as neurostimulation to treat other parts of the body, such as the retina, the peripheral nervous system.

Various embodiments of neurological stimulation devices and techniques have been described herein. These embodiments are given by way of example and are not intended to limit the scope of the present invention. It should be appreciated, moreover, that the various features of the embodiments that have been described may be combined in various ways to produce numerous additional embodiments.

While this invention has been particularly shown and described with references to preferred embodiments thereof, it will be understood by those skilled in the art that various changes in form and details may be made therein without departing from the scope of the invention encompassed by the appended claims.

What is claimed is:

1. An apparatus for stimulating a neurological target, comprising:
    at least one microelectrode positionable at the neurological target;
    an impedance analyzer in electrical communication with each of the at least one microelectrodes, the impedance analyzer measures respective electrical impedance values indicative of a microelectrode-tissue interface at each of a plurality of different frequencies for each of the at least one microelectrodes;
    a preferred-frequency detector in communication with the impedance analyzer, the preferred-frequency detector detects from among the electrical impedance values measured at each of the at least one microelectrodes, a respective preferred peak resistance frequency; and
    a stimulation source in communication with at least one of the at least one microelectrodes, the stimulation source stimulates the neurological target at the respective preferred peak resistance frequency.

2. The apparatus of claim 1, wherein each of the at least one microelectrodes is a microelectrode having dimensions approximating those of a cell, or a group of cells, of the neurological target.

3. The apparatus of claim 1, comprising a plurality of electrical microelectrodes.

4. The apparatus of claim 3, wherein the plurality of electrical microelectrodes is disposed along an elongated support structure.

5. The apparatus of claim 1, further comprising at least one electrical filter in electrical communication between the stimulation source and at least one of the at least one microelectrodes.

6. The apparatus of claim 5, wherein the at least one electrical filters is tunable to include the respective preferred peak resistance frequency for the at least one of the at least one microelectrodes.

7. The apparatus of claim 6, further comprising a respective electrical filter in electrical communication between the stimulation source and each of the at least one microelectrodes.

8. The apparatus of claim 1, the stimulation source further comprises a pulse generator and an electrical filter in electrical communication between the pulse generator and at least one of the at least one microelectrodes.

9. The apparatus of claim 1, further comprising a signal router configured to selectively establish a signal path between each of the at least one microelectrodes and at least one of the impedance analyzer and the stimulation source.

10. The apparatus of claim 9, further comprising:
- a sensor in communication with each of the at least one microelectrodes, the sensor configured to measure electrical signals indicative of neuronal activity; and
- a controller in communication with at least the sensor and the signal router, the controller configured to selectively establish a signal path between at least one of the microelectrodes and the stimulation source responsive to electrical signals measured by the sensor.

* * * * *